US012799448B2

(12) United States Patent
Tanabe et al.

(10) Patent No.: US 12,799,448 B2
(45) Date of Patent: Nov. 17, 2026

(54) ERYTHROCYTE REMOVAL DEVICE, MONONUCLEAR CELL COLLECTOR, CELL CULTURE DEVICE, CELL CULTURE SYSTEM, CELL CULTURE METHOD, AND METHOD FOR COLLECTING MONONUCLEAR CELLS

(71) Applicants: I Peace, Inc., Palo Alto, CA (US); FANUC CORPORATION, Yamanashi (JP)

(72) Inventors: Koji Tanabe, Palo Alto, CA (US); Ryoji Hiraide, Kyoto (JP); Kiyonori Inaba, Yamanashi (JP); Kazunori Ban, Yamanashi (JP); Satoshi Kinoshita, Yamanashi (JP)

(73) Assignees: I Peace, Inc., Palo Alto, CA (US); FANUC CORPORATION, Yamanashi (JP)

( * ) Notice: Subject to any disclaimer, the term of this patent is extended or adjusted under 35 U.S.C. 154(b) by 852 days.

(21) Appl. No.: 17/596,412

(22) PCT Filed: Jun. 10, 2020

(86) PCT No.: PCT/JP2020/022843

§ 371 (c)(1),
(2) Date: Dec. 9, 2021

(87) PCT Pub. No.: WO2020/250929

PCT Pub. Date: Dec. 17, 2020

(65) Prior Publication Data

US 2022/0306981 A1 Sep. 29, 2022

Related U.S. Application Data

(60) Provisional application No. 62/859,320, filed on Jun. 10, 2019.

(51) Int. Cl.
*C12M 1/00* (2006.01)
*C12M 1/12* (2006.01)
(Continued)

(52) U.S. Cl.
CPC ............ *C12M 47/04* (2013.01); *C12M 23/34* (2013.01); *C12M 25/10* (2013.01); *C12M 33/04* (2013.01); *C12M 41/12* (2013.01)

(58) Field of Classification Search
CPC ...... C12M 47/04; C12M 23/34; C12M 25/10; C12M 33/04; C12M 41/12
See application file for complete search history.

(56) References Cited

U.S. PATENT DOCUMENTS 3,700,555 A 10/1972 Widmark et al.
2003/0143727 A1 7/2003 Chang
(Continued)

FOREIGN PATENT DOCUMENTS

JP S47-008441 A 5/1972
JP S57-005240 U 1/1982
(Continued)

OTHER PUBLICATIONS

International Search Report issued in PCT/JP2020/022843; mailed Sep. 1, 2020.
(Continued)

*Primary Examiner* — Michael A Marcheschi
*Assistant Examiner* — Ashley Lopezlira
(74) *Attorney, Agent, or Firm* — Studebaker Brackett PLLC

(57) ABSTRACT

Provided is an erythrocyte removal device 100 including a blood container 10 that holds blood and an erythrocyte removal vessel 11 that at least partially removes erythrocytes from blood.

19 Claims, 18 Drawing Sheets

(51) Int. Cl.

| | |
|---|---|
| ***C12M 1/26*** | (2006.01) |
| ***C12M 1/34*** | (2006.01) |

(56) References Cited

U.S. PATENT DOCUMENTS

| | | | | |
|---|---|---|---|---|
| 2005/0239196 | A1 | 10/2005 | Yanai et al. | |
| 2009/0068742 | A1 | 3/2009 | Yamanaka | |
| 2009/0311775 | A1* | 12/2009 | Kocourek | B01F 33/50111 435/289.1 |
| 2015/0306641 | A1 | 10/2015 | Suzuki et al. | |
| 2016/0206512 | A1* | 7/2016 | Chhikara | A61J 1/2096 |
| 2016/0348052 | A1 | 12/2016 | Lin et al. | |
| 2017/0002305 | A1* | 1/2017 | Shevitz | B01D 61/58 |
| 2018/0320122 | A1* | 11/2018 | Blanchard | C12M 1/22 |
| 2019/0382706 | A1 | 12/2019 | Tanabe et al. | |
| 2020/0123484 | A1* | 4/2020 | Tseng | C12M 23/16 |
| 2021/0197196 | A1* | 7/2021 | Glieberman | C12M 23/16 |
| 2021/0222103 | A1* | 7/2021 | Martin | C12M 23/20 |

FOREIGN PATENT DOCUMENTS

| | | | | |
|---|---|---|---|---|
| JP | S57-007547 | U | 1/1982 | |
| JP | H4-356184 | A | 12/1992 | |
| JP | 2003-180334 | A | 7/2003 | |
| JP | 2004-073084 | A | 3/2004 | |
| JP | 2005-279507 | A | 10/2005 | |
| JP | 4183742 | B1 | 11/2008 | |
| JP | 2010-200693 | A | 9/2010 | |
| JP | 2012-034725 | A | 2/2012 | |
| JP | 2014-114997 | A | 6/2014 | |
| JP | 2016-524987 | A | 8/2016 | |
| WO | 2013/175797 | A1 | 11/2013 | |
| WO | WO-2016185221 | A1 * | 11/2016 | A61M 5/148 |
| WO | WO-2018087558 | A1 * | 5/2018 | C12M 23/26 |
| WO | 2018/154788 | A1 | 8/2018 | |

OTHER PUBLICATIONS

International Preliminary Report On Patentability (Chapter II) with Annex issued in PCT/JP2020/022843; completed Oct. 6, 2021.

* cited by examiner (a)

(b)

(b)

(a)

ERYTHROCYTE REMOVAL DEVICE, MONONUCLEAR CELL COLLECTOR, CELL CULTURE DEVICE, CELL CULTURE SYSTEM, CELL CULTURE METHOD, AND METHOD FOR COLLECTING MONONUCLEAR CELLS

This application claims benefit to PCT application PCT/JP2020/022843, filed Jun. 10, 2020; which claims benefit to U.S. provisional application 62/859,320, filed Jun. 10, 2019; said applications incorporated herein by reference.

TECHNICAL FIELD

The present invention relates to cell technology and relates to an erythrocyte removal device, a mononuclear cell collector, a cell culture device, a cell culture system, a cell culture method, and a method for collecting mononuclear cells.

BACKGROUND ART

Embryonic stem cells (ES cells) are stem cells established from early mouse or human embryos. ES cells exhibit a pluripotency that enables differentiation into any of the cells present in an organism. At present, human ES cells can be used in cell transplantation therapy for a number of diseases, e.g., Parkinson's disease, juvenile onset diabetes, and leukemia. However, there are also barriers to ES cell transplantation. In particular, ES cell transplantation can induce an immunorejection similar to the rejection that occurs following unsuccessful organ transplantation. The use of ES cells that have been established by the destruction of human embryos has also received much criticism and opposition from an ethical standpoint.

With these circumstances as background, Professor Shinya Yamanaka of Kyoto University succeeded in establishing induced pluripotent stem cells (iPS cells) by the introduction of the four genes OCT3/4, KLF4, c-MYC, and SOX2 into somatic cells. Professor Yamanaka received the Nobel Prize in Physiology or Medicine in 2012 as a result (see, for example, Patent Documents 1 and 2). iPS cells are ideal pluripotent cells which are free of rejection reactions and ethical issues. iPS cells are therefore considered promising for use in cell transplantation therapy.

CITATION LIST

Patent Documents

Patent Document 1: Japanese Patent No. 4183742
Patent Document 2: Japanese Patent Application Laid-open No. 2014-114997

SUMMARY

Technical Problem iPS cells can be induced from blood cells. A technology is desired that can efficiently process blood cells without being limited to application to iPS cell induction. A device is also desired that can efficiently culture various types of cells without being limited to iPS cells. An object of the present invention is therefore to provide an erythrocyte removal device, a mononuclear cell collector, a cell culture device, a cell culture system, a cell culture method, and a method for collecting mononuclear cells.

Solution to Problem

An aspect of the present invention provides an erythrocyte removal device comprising a blood container that holds blood, an erythrocyte removal vessel that receives blood from the blood container and at least partially removes erythrocytes from the blood, and a flow channel for transporting at least the blood from the blood container to the erythrocyte removal vessel.

The interior of the flow channel for transporting the blood from the blood container to the erythrocyte removal vessel in the aforementioned erythrocyte removal device may be capable of being closed off from outside air.

The aforementioned erythrocyte removal device may further comprise: a mononuclear cell collector that receives, from the erythrocyte removal vessel, treated blood from which the erythrocytes have been at least partially removed, and that collects mononuclear cells from the treated blood; and a flow channel for transporting, from the erythrocyte removal vessel to the mononuclear cell collector, at least the treated blood from which the erythrocytes have been at least partially removed.

The gas in the interior of the erythrocyte removal vessel in the aforementioned erythrocyte removal device may be removable.

The aforementioned erythrocyte removal device may further comprise a flow channel that carries treated blood from which erythrocytes have been at least partially removed, wherein the interior of the flow channel that carries treated blood from which erythrocytes have been at least partially removed, may be capable of being closed off from outside air.

The gas in the interior of the mononuclear cell collector in the aforementioned erythrocyte removal device may be removable.

The interior of the blood container and the interior of the erythrocyte removal vessel in the aforementioned erythrocyte removal device may be capable of being closed off from outside air.

The interior of the mononuclear cell collector in the aforementioned erythrocyte removal device may be capable of being closed off from the outside air.

The closed space including the interior of the blood container and the interior of the erythrocyte removal vessel in the aforementioned erythrocyte removal device may not exchange gas with the outside.

The blood container and the erythrocyte removal vessel in the aforementioned erythrocyte removal device may be embedded.

At least a portion of the blood container and/or at least a portion of the erythrocyte removal vessel in the aforementioned erythrocyte removal device may be formed by inscribing in a member.

The mononuclear cell collector in the aforementioned erythrocyte removal device may be embedded.

At least a portion of the mononuclear cell collector in the aforementioned erythrocyte removal device may be formed by inscribing in a member.

Blood may be mixed in the erythrocyte removal vessel in the aforementioned erythrocyte removal device with at least one of an erythrocyte sedimentation agent and an erythrocyte removal agent.

The aforementioned erythrocyte removal device may further comprise an erythrocyte treatment agent container that holds at least one of an erythrocyte sedimentation agent and an erythrocyte removal agent, and the erythrocyte removal vessel may receive from the erythrocyte treatment agent container at least one of an erythrocyte sedimentation agent and an erythrocyte removal agent.

The aforementioned erythrocyte removal device may further comprise a mixer that mixes blood with at least one of an erythrocyte sedimentation agent and an erythrocyte removal agent, and the erythrocyte removal vessel may receive from the mixer a blood that has been mixed with the at least one of an erythrocyte sedimentation agent and an erythrocyte removal agent.

The mixer in the aforementioned erythrocyte removal device may comprise a bent flow channel that carries a mixture of blood and at least one of an erythrocyte sedimentation agent and an erythrocyte removal agent.

The aforementioned erythrocyte removal device may further comprise a flow channel for transporting at least blood from the blood container to the erythrocyte removal vessel.

The aforementioned erythrocyte removal device may comprise a vacuum container, the interior of which can be placed under a vacuum, and which is connected to a flow channel for transporting at least blood from the blood container to the erythrocyte removal vessel.

The aforementioned erythrocyte removal device may further comprise: an erythrocyte treatment agent container that holds the at least one of an erythrocyte sedimentation agent and an erythrocyte removal agent; and a flow channel for at least transporting, from the erythrocyte treatment agent container to the erythrocyte removal vessel, the at least one of an erythrocyte sedimentation agent and an erythrocyte removal agent.

The aforementioned erythrocyte removal device may further comprise a fluid machinery for transporting at least blood from the blood container to the erythrocyte removal vessel.

The blood container in the aforementioned erythrocyte removal device may be capable of undergoing a change in the volume of the blood container.

The erythrocyte removal vessel in the aforementioned erythrocyte removal device may be capable of undergoing a change in the volume of the erythrocyte removal vessel.

The mononuclear cell collector in the aforementioned erythrocyte removal device may be capable of undergoing a change in the volume of the mononuclear cell collector.

The erythrocyte treatment agent container in the aforementioned erythrocyte removal device may be capable of undergoing a change in the volume of the erythrocyte treatment agent container.

In the aforementioned erythrocyte removal device, the erythrocytes may be sedimented in the erythrocyte removal vessel and a supernatant in the erythrocyte removal vessel may be transported, as the treated blood from which the erythrocytes have been at least partially removed, to the mononuclear cell collector.

The aforementioned erythrocyte removal device may further comprise a flow channel for transporting, from the erythrocyte removal vessel to the mononuclear cell collector, at least treated blood from which erythrocytes have been at least partially removed.

The aforementioned erythrocyte removal device may further comprise a fluid machinery for transporting, from the erythrocyte removal vessel to the mononuclear cell collector, at least treated blood from which erythrocytes have been at least partially removed.

The treated blood from which the erythrocytes have been at least partially removed, may be diluted in the mononuclear cell collector in the aforementioned erythrocyte removal device.

The mononuclear cells may be sedimented in the mononuclear cell collector in the aforementioned erythrocyte removal device.

Platelets may be suspended in the dilution of the treated blood in the aforementioned erythrocyte removal device.

In the aforementioned erythrocyte removal device, erythrocytes may be hemolyzed in the dilution of the treated blood by erythrocyte removal agent.

The aforementioned erythrocyte removal device may further comprise a liquid diluent container that holds liquid diluent for diluting the treated blood from which the erythrocytes have been at least partially removed.

The liquid diluent in the aforementioned erythrocyte removal device may be a buffer solution.

The liquid diluent container in the aforementioned erythrocyte removal device may be capable of undergoing a change in the volume of the liquid diluent container.

After the mononuclear cells have sedimented in the mononuclear cell collector, the supernatant in the mononuclear cell collector may be removed in the aforementioned erythrocyte removal device.

In the aforementioned erythrocyte removal device, the platelets suspended in the supernatant may be removed by removal of the supernatant.

In the aforementioned erythrocyte removal device, a component of the hemolyzed erythrocytes suspended in the supernatant may be removed by removal of the supernatant.

In the aforementioned erythrocyte removal device, a first opening may be provided at the bottom of the mononuclear cell collector and a second opening may be provided at a position higher than that of the first opening in a direction of gravitational force.

In the aforementioned erythrocyte removal device, the bottom of the mononuclear cell collector may be funnel shaped, a first opening may be disposed at the tip of the funnel-shaped bottom, and a second opening may be disposed in a side of the funnel-shaped bottom.

When, in the aforementioned erythrocyte removal device, treated blood from which erythrocytes have been at least partially removed, is introduced into the mononuclear cell collector, the mononuclear cells may accumulate at the bottom and the supernatant may be discharged through the second opening.

The platelets suspended in the supernatant may be removed in the aforementioned erythrocyte removal device by discharging the supernatant.

In the aforementioned erythrocyte removal device, a component of the hemolyzed erythrocytes suspended in the supernatant may be removed by discharge of the supernatant.

The aforementioned erythrocyte removal device may further comprise a mononuclear cell suction device that suctions mononuclear cells through the first opening.

In the aforementioned erythrocyte removal device, the size of the first opening may be established such that, when the mononuclear cells are not suctioned by the mononuclear cell suction device, the mononuclear cells pack the first opening.

The aforementioned erythrocyte removal device may further comprise a flow channel for transporting a fluid in the erythrocyte removal vessel to the blood container.

The aforementioned erythrocyte removal device may further comprise at least one of a fluid machinery for transporting at least blood from the blood container to the erythrocyte removal vessel and a fluid machinery for transporting a fluid within the erythrocyte removal vessel to the blood container.

The aforementioned erythrocyte removal vessel may further comprise a flow channel for transporting a fluid within the mononuclear cell collector to the erythrocyte removal vessel.

The aforementioned erythrocyte removal device may further comprise at least one of a fluid machinery for transporting, from the erythrocyte removal vessel to the mononuclear cell collector, at least the treated blood from which the erythrocytes have been at least partially removed, and a fluid machinery for transporting a fluid in the mononuclear cell collector to the erythrocyte removal vessel.

An aspect of the present invention provides a mononuclear cell collector comprising a collection container that holds a mononuclear cell-containing solution, wherein the bottom of the collection container is funnel shaped, a first opening is provided at the tip of the funnel-shaped bottom, and a second opening is provided in a side of the funnel-shaped bottom.

When the solution is introduced into the collection container in the aforementioned mononuclear cell collector, the mononuclear cells may accumulate at the tip of the funnel-shaped bottom and the solution may be discharged through the second opening.

The aforementioned mononuclear cell collector may further comprise a mononuclear cell suction device that suctions the mononuclear cells that have accumulated at the tip of the funnel-shaped bottom.

In the aforementioned mononuclear cell collector, the size of the first opening may be established such that, when the mononuclear cells are not suctioned by the mononuclear cell suction device, the mononuclear cells pack the first opening.

An aspect of the present invention provides a cell culture device comprising a cell culture vessel for culturing cells; and a variable-volume container connected to the cell culture vessel, wherein a fluid can move within the cell culture vessel and the variable-volume container.

For the variable-volume container, the aforementioned cell culture device may comprise at least a first variable-volume container and a second variable-volume container.

In the aforementioned cell culture device, in the case where fluid in the cell culture vessel is transferred into the first variable-volume container, the volume of the first variable-volume container may expand and the volume of the second variable-volume container may contract.

In the aforementioned cell culture device, in the case where fluid in the first variable-volume container is transferred into the cell culture vessel, the volume of the first variable-volume container may contract and the volume of the second variable-volume container may expand.

In the aforementioned cell culture device, in the case where fluid in the second variable-volume container is transferred into the cell culture vessel, the volume of the second variable-volume container may contract and the volume of the first variable-volume container may expand.

In the aforementioned cell culture device, the interior of the cell culture vessel, the interior of the first variable-volume container, and the interior of the second variable-volume container may be capable of being closed off from outside air.

In the aforementioned cell culture device, the cell culture vessel, the first variable-volume container, and the second variable-volume container may be embedded.

In the aforementioned cell culture device, at least a portion of the cell culture device, at least a portion of the first variable-volume container, and at least a portion of the second variable-volume container may be formed by inscribing in a member.

In the aforementioned cell culture device, the first variable-volume container may hold a substance and the substance may contact the cells by the movement of a fluid.

In the aforementioned cell culture device, the substance may be an inducing factor and the inducing factor may be introduced into cells by the movement of a fluid.

The aforementioned cell culture device may further comprise a fluid machinery for transferring fluid within the cell culture vessel to the first variable-volume container.

The aforementioned cell culture device may further comprise a fluid machinery for transferring a fluid within the cell culture vessel to the second variable-volume container.

The aforementioned cell culture device may further comprise a flow channel for supplying cells into the cell culture vessel.

The aforementioned cell culture device may further comprise a flow channel for supplying a culture solution, this flow channel being connected to the flow channel for supplying cells into the cell culture vessel.

In the aforementioned cell culture device, culture solution and cells may be mixed in the flow channel for supplying cells into the cell culture vessel and a cell-containing culture solution may be supplied to the cell culture vessel.

In the aforementioned cell culture device, in the case where cells are introduced into the cell culture vessel from the flow channel for supplying cells, the volume of at least one of the first variable-volume container and the second variable-volume container may expand.

The aforementioned cell culture device may further comprise a fluid machinery for supplying cells into the cell culture vessel.

The cells in the aforementioned cell culture device may be somatic cells or stem cells.

The aforementioned cell culture device may further comprise a fluid container that holds fluid to be supplied into the cell culture vessel.

The fluid in the aforementioned cell culture device may be a somatic cell culture medium or a stem cell culture medium.

The stem cell culture medium in the aforementioned cell culture device may be an induction culture medium, an expansion culture medium, or a maintenance culture medium.

In the aforementioned cell culture device, in the case where fluid is supplied from the fluid container into the cell culture vessel, the volume of at least either of the first variable-volume container and the second variable-volume container may expand.

The aforementioned cell culture device may further comprise a fluid machinery for supplying fluid into the cell culture vessel.

The aforementioned cell culture device may further comprise a temperature control element that controls the temperature in the cell culture vessel.

The cells in the cell culture vessel may be adherent cultured in the aforementioned cell culture device.

The interior of the cell culture vessel in the aforementioned cell culture device may be coated with a cell adhesion coating agent.

The cells in the cell culture vessel may be suspension cultured in the aforementioned cell culture device.

The aforementioned cell culture device may further comprise a hollow fiber membrane disposed in the cell culture vessel.

Cells may be cultured on the inside of the hollow fiber membrane in the aforementioned cell culture device.

The cells in the cell culture vessel may be transferrable to a variable-volume container in the aforementioned cell culture device.

The aforementioned cell culture device may further comprise: a flow channel connected to the cell culture vessel; and a fluid machinery disposed in the flow channel, wherein at least one of passaging of cells and expansion cell culture may be carried out by suctioning the cells in the cell culture vessel into the flow channel and returning the cells in the flow channel to the cell culture vessel by the fluid machinery.

The flow channel in the aforementioned cell culture device may have a structure that dissociates cell masses.

An aspect of the present invention provides a cell culture system comprising a mononuclear cell collector that collects mononuclear cells from blood; and a cell culture vessel that receives mononuclear cells from the mononuclear cell collector.

In the aforementioned cell culture system, the mononuclear cell collector may receive treated blood from which erythrocytes have been at least partially removed, and may collect mononuclear cells from the treated blood.

The aforementioned cell culture system may further comprise an erythrocyte removal vessel for supplying, to the mononuclear cell collector, treated blood from which the erythrocytes have been at least partially removed.

The aforementioned cell culture system may further comprise a blood container for supplying, to the erythrocyte removal vessel, blood prior to the at least partial removal of the erythrocytes.

The aforementioned cell culture system may comprise a variable-volume container that is connected to the cell culture vessel, wherein the volume of the variable-volume container may expand in the case where fluid in the cell culture vessel is transferred to the variable-volume container.

The aforementioned cell culture system may comprise a first variable-volume container connected to the cell culture vessel and a second variable-volume container connected to the cell culture vessel, wherein, in the case where fluid in the cell culture vessel is transferred to the first variable-volume container, the volume of the first variable-volume container may expand and the volume of the second variable-volume container may contract.

In the aforementioned cell culture system, the interior of the mononuclear cell collector and the interior of the cell culture vessel may be capable of being closed off from outside air.

The interior of the erythrocyte removal vessel in the aforementioned cell culture system may be capable of being closed off from outside air.

The interior of the blood container in the aforementioned cell culture system may be capable of being closed off from outside air.

In the aforementioned cell culture system, the interior of the first variable-volume container and the interior of the second variable-volume container may be capable of being closed off from outside air.

The blood container, erythrocyte removal vessel, mononuclear cell collector, and cell culture vessel in the aforementioned cell culture system may be embedded.

In the aforementioned cell culture system, at least a portion of the blood container, at least a portion of the erythrocyte removal vessel, at least a portion of the mononuclear cell collector, and at least a portion of the cell culture vessel may be formed by inscribing in a member.

The first variable-volume container and the second variable-volume container in the aforementioned cell culture system may be embedded.

In the aforementioned cell culture system, at least a portion of the first variable-volume container and at least a portion of the second variable-volume container may be formed by inscribing in a member.

In the aforementioned cell culture system, the interior of the first variable-volume container and the interior of the second variable-volume container may not exchange gas with the outside.

An aspect of the present invention provides a cell culture method comprising introducing a factor into cells in a cell culture vessel and culturing the factor-introduced cells in the same cell culture vessel as the cell culture vessel.

In the aforementioned cell culture method, the cell culture vessel may be closed during the introduction of the factor into the cells and the culture of the factor-introduced cells.

In the aforementioned cell culture method, a variable-volume container may be connected to the cell culture vessel and a fluid may be moved within the cell culture vessel and the variable-volume container.

A factor may be supplied from the variable-volume container in the aforementioned cell culture method.

In the aforementioned cell culture method, cells in a second state may be induced from factor-introduced cells in a first state in the same cell culture vessel.

In the aforementioned cell culture method, the first state may be a differentiated state and the second state may be an undifferentiated state.

In the aforementioned cell culture method, the first state may be a dedifferentiated state and the second state may be a differentiated state.

In the aforementioned cell culture method, the first state may be a dedifferentiated state and the second state may be a dedifferentiated state different from the first state.

The cells in the first state may be somatic cells in the aforementioned cell culture method.

The cells in the first state may be blood cells in the aforementioned cell culture method.

The cells in the first state may be mononuclear cells in the aforementioned cell culture method.

The cells in the second state may be stem cells in the aforementioned cell culture method.

The cells in the second state may be iPS cells in the aforementioned cell culture method.

The cells in the first state may be stem cells in the aforementioned cell culture method.

The cells in the first state may be iPS cells in the aforementioned cell culture method.

The cells in the second state may be somatic cells in the aforementioned cell culture method.

In the aforementioned cell culture method, the cells in the first state may be somatic cells and the cells in the second state may be somatic cells different from the cells in the first state.

In the aforementioned cell culture method, the cells in the first state may be blood cells from which erythrocytes have been at least partially removed.

In the aforementioned cell culture method, the cells in the first state may be blood cells from which platelets have been at least partially removed.

The factor in the aforementioned cell culture method may be a factor that induces cells in the second state from cells in the first state.

The factor in the aforementioned cell culture method may be a factor that induces a prescribed cellular state.

The factor in the aforementioned cell culture method may be an initialization factor.

The factor in the aforementioned cell culture method may be a differentiation induction factor.

In the aforementioned cell culture method, cells may be passaged or expansion cultured by collecting factor-introduced cells from the cell culture vessel and returning the cells to the same cell culture vessel as the cell culture vessel.

An aspect of the present invention provides a method for collecting mononuclear cells, comprising treating blood to prepare a treated blood from which erythrocytes have been at least partially removed; diluting the treated blood; sedimenting the mononuclear cells contained in the diluted treated blood; removing the supernatant of the diluted treated blood; and collecting the mononuclear cells.

In the aforementioned method for collecting mononuclear cells, the treated blood is prepared in an erythrocyte removal vessel; dilution of the treated blood, sedimentation of the mononuclear cells, and removal of the supernatant are performed in a mononuclear cell collector; and the erythrocyte removal vessel and mononuclear cell collector are closed.

In the aforementioned method for collecting mononuclear cells, the blood may be treated with an erythrocyte sedimentation agent or an erythrocyte removal agent.

In the aforementioned method for collecting mononuclear cells, the treated blood may be diluted with a phosphate buffer solution.

In the aforementioned method for collecting mononuclear cells, the supernatant of the diluted treated blood may contain platelets.

In the aforementioned method for collecting mononuclear cells, the collected mononuclear cells may be in a condition of at least partial erythrocyte removal.

In the aforementioned method for collecting mononuclear cells, at least partial platelet has been removed from the collected mononuclear cells.

Advantageous Effects of Invention

The present invention makes it possible to provide an erythrocyte removal device, a mononuclear cell collector, a cell culture device, a cell culture system, a cell culture method, and a method for collecting mononuclear cells.

DESCRIPTION OF EMBODIMENTS

Embodiments of the present invention are described in the following. In the following description of the drawings, the same or similar parts are represented by the same or similar reference signs. However, the drawings are schematic. Therefore, the specific dimensions and so forth should be determined in light of the explanations that follow. In addition, elements having different dimensional relationships and/or ratios from each other are of course also present between the drawings.

First Embodiment

Figure 1:
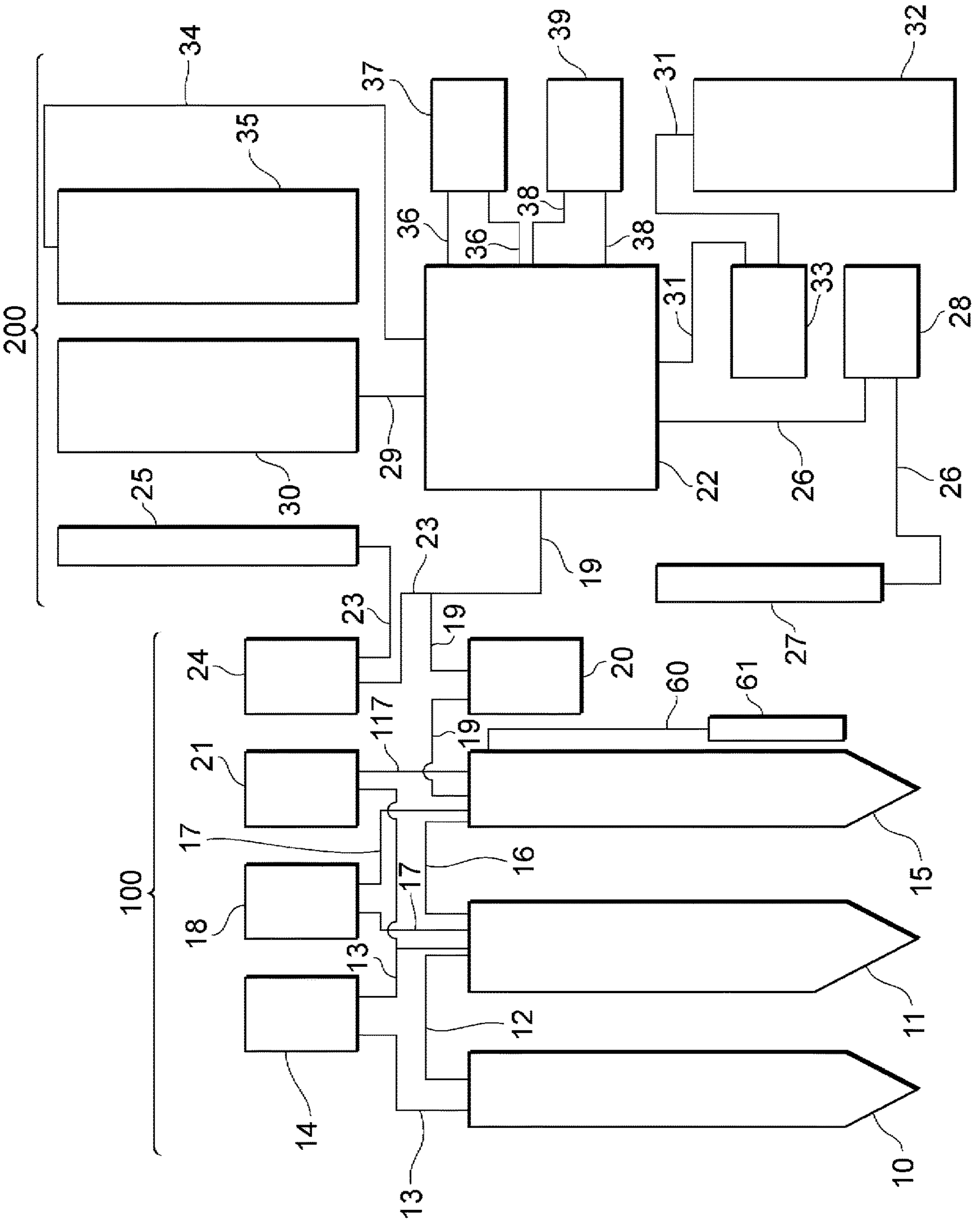
FIG. 1 is a schematic diagram of a cell culture system according to a first embodiment.

As shown in FIG. 1, an erythrocyte removal device 100 according to the first embodiment comprises a blood container 10, which holds blood, and an erythrocyte removal vessel 11, which receives blood from the blood container 10 and at least partially removes the erythrocytes from the blood.

The blood container 10 holds blood in its interior. The blood container 10 can have a structure configured to make the interior closed from the outside air. The closed space comprising the interior of the blood container 10 may be configured such that gas exchange with the outside does not occur. The blood container 10 may be inset and embedded in a gas-impermeable material. At least a portion of the blood container 10 may be formed by inscribing in a member. At least a portion of the blood container 10 may be formed by inscribing in a member and overlaying the recess.

The blood container 10 may be capable of undergoing a change in the volume of the blood container 10.

The erythrocyte removal vessel 11 holds in its interior, for example, an erythrocyte sedimentation agent or an erythrocyte removal agent. The erythrocyte removal vessel 11 may have a structure configured to make the interior closed from the outside air. The closed space comprising the interior of the erythrocyte removal vessel 11 may be configured such that the exchange of gas, viruses, microorganisms, impurities, and so forth, with the outside does not occur. The erythrocyte removal vessel 11 may be inset and embedded in a gas-impermeable material. At least a portion of the erythrocyte removal vessel 11 may be formed by inscribing in a member. At least a portion of the erythrocyte removal vessel 11 may be formed by inscribing in a member and overlaying the recess. The erythrocyte removal vessel 11 may be capable of undergoing a change in the volume of the erythrocyte removal vessel 11.

A flow channel 13 for transporting blood from the blood container 10 to the erythrocyte removal vessel 11 is disposed between the blood container 10 and the erythrocyte removal vessel 11. The flow channel 13 may have a structure configured to make the interior closed from the outside air. The closed space comprising the interior of the flow channel 13 may be configured such that the exchange of gas, viruses, microorganisms, impurities, and so forth, with the outside does not occur. The flow channel 13 may be inset and embedded in a gas-impermeable material. At least a portion of the flow channel 13 may be formed by inscribing in a member. At least a portion of the flow channel 13 may be formed by inscribing in a member and overlaying the recess.

A flow channel 12 for transporting a fluid, e.g., a gas such as air, from the erythrocyte removal vessel 11 to the blood container 10 is disposed between the blood container 10 and the erythrocyte removal vessel 11. The flow channel 12 may have a structure configured to make the interior closed from the outside air. The closed space comprising the interior of the flow channel 12 can be configured such that the exchange of gas, viruses, microorganisms, impurities, and so forth, with the outside does not occur. The flow channel 12 may be inset and embedded in a gas-impermeable material. At least a portion of the flow channel 12 may be formed by inscribing in a member. At least a portion of the flow channel 12 may be formed by inscribing in a member and overlaying the recess.

The blood container 10 is connected with the flow channel 12 and with the flow channel 13 by a connector. The connector may be an aseptic connector. The connector may be a needleless connector. The needleless connector may be a split septum type or may be a mechanical valve type.

A fluid machinery 14, e.g., a pump, for transferring fluid within the flow channel 13 may be disposed in the flow channel 13. A fluid machinery may be disposed in the flow channel 12, or fluid machineries may be disposed in both the flow channel 12 and the flow channel 13. In the present disclosure, "fluid" encompasses both gases and liquids.

A positive displacement pump can be used as the fluid machinery 14. The positive displacement pump can be exemplified by reciprocating pumps such as piston pumps, plunger pumps, and diaphragm pumps, and by rotary pumps such as gear pumps, vane pumps, and screw pumps. The diaphragm pumps can be exemplified by tubing pumps and piezoelectric (piezo) pumps. Tubing pumps are also called peristaltic pumps. A microfluidic chip module that combines several types of pumps may also be used. The same also applies for the other fluid machineries in the present disclosure. By using a sealed pump, e.g., a peristaltic pump, tubing pump, diaphragm pump, and so forth, the fluid can be transported without the pump being in direct contact with the fluid in the fluid channel.

In the case where a gas and an erythrocyte sedimentation agent have been preliminarily filled into the erythrocyte removal vessel 11, when the fluid machinery 14 suctions the blood in the blood container 10 via the flow channel 13 and supplies the suctioned blood into the erythrocyte removal vessel 11, the gas in the erythrocyte removal vessel 11 is pushed by the pressure and is transported via the flow channel 12 into the blood container 10. Proceeding in this manner, the pressure in the blood container 10 and the erythrocyte removal vessel 11 can be equilibrated by transporting the blood in the blood container 10 into the erythrocyte removal vessel 11 and transporting the gas in the erythrocyte removal vessel 11 into the blood container 10.

The fluid machinery 14 may suction, via the flow channel 13, the gas in the erythrocyte removal vessel 11 and may supply the suctioned gas into the blood container 10. In this case, the blood in the blood container 10 is pushed by pressure and is transported via the flow channel 12 into the erythrocyte removal vessel 11. Proceeding in this manner makes it possible to also transport the blood in the blood container 10 into the erythrocyte removal vessel 11 through the removal of the gas in the erythrocyte removal vessel 11.

The blood transported into the erythrocyte removal vessel 11 comes into contact with the erythrocyte sedimentation agent or erythrocyte removal agent in the erythrocyte removal vessel 11. The fluid machinery 14 may stir the blood by repeating the following: suctioning fluid from within the erythrocyte removal vessel 11 and delivering the fluid into the erythrocyte removal vessel 11. In the case where an erythrocyte sedimentation agent is contained in the erythrocyte removal vessel 11, the erythrocytes are at least partially removed from the blood through the sedimentation of the erythrocytes in the erythrocyte removal vessel 11. In the case where an erythrocyte removal agent is contained in the erythrocyte removal vessel 11, the erythrocytes are at least partially removed from the blood through hemolysis of the erythrocytes in the erythrocyte removal vessel 11.

The erythrocyte removal device 100 may further comprise a mononuclear cell collector 15 that receives, from the erythrocyte removal vessel 11, treated blood from which erythrocytes have been at least partially removed, and that collects mononuclear cells from the treated blood. The mononuclear cell collector 15 may have a structure configured to make the interior closed from the outside air. The closed space comprising the interior of the mononuclear cell collector 15 can be configured such that the exchange of gas, viruses, microorganisms, impurities, and so forth, with the outside does not occur. The mononuclear cell collector 15 may be inset and embedded in a gas-impermeable material. At least a portion of the mononuclear cell collector 15 may be formed by inscribing in a member. At least a portion of the mononuclear cell collector 15 may be formed by inscribing in a member and overlaying the recess. The mononuclear cell collector 15 may be capable of undergoing a change in the volume of the mononuclear cell collector 15.

Figure 2:
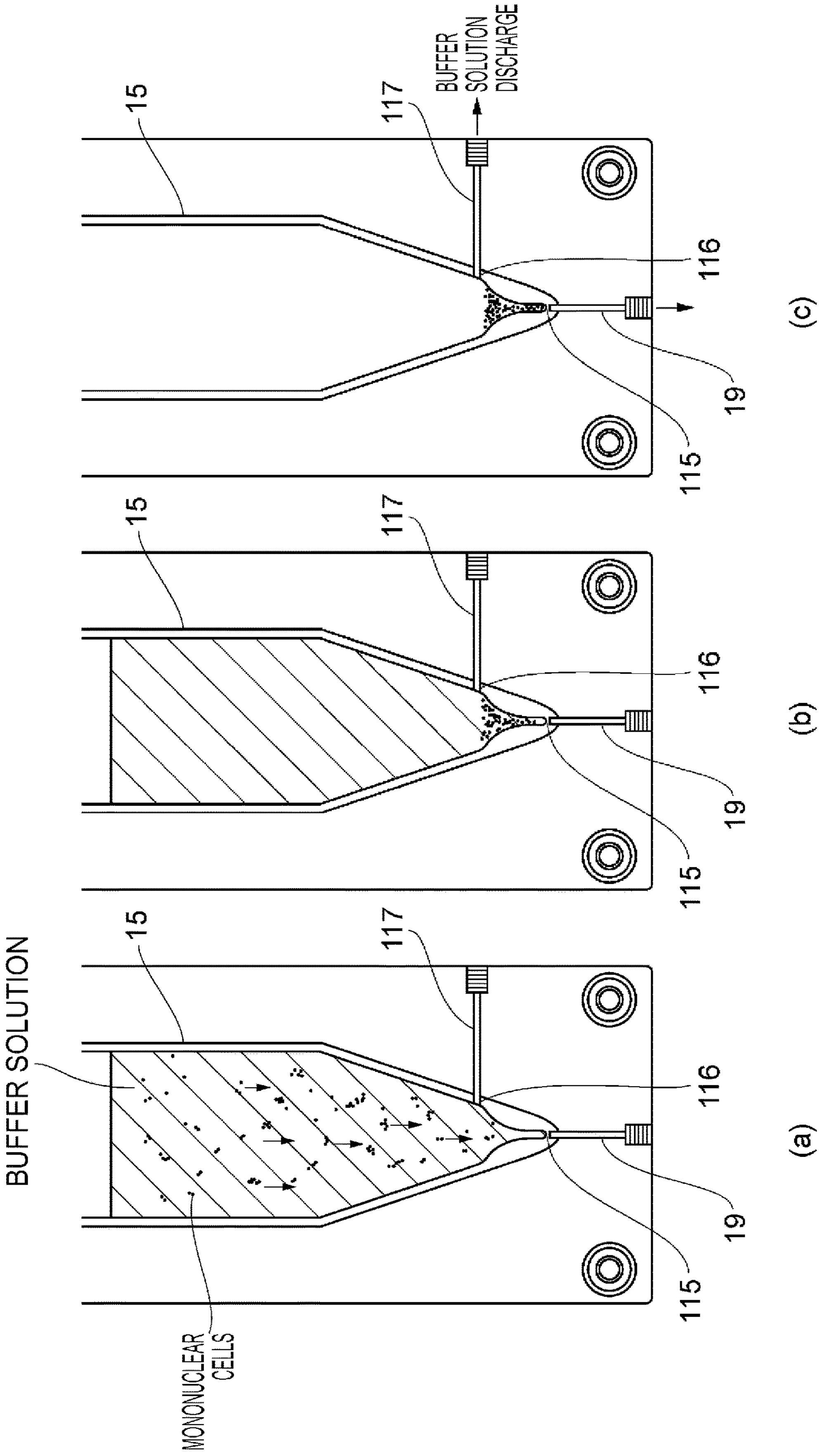
FIG. 2 is a schematic diagram of a mononuclear cell collector according to the first embodiment.

As shown in FIG. 2, for example, a first opening 115 is provided at the bottom of the mononuclear cell collector 15 and a second opening 116 is provided in a side of the mononuclear cell collector 15. The position of the first opening 115 is below that of the second opening 116 in the direction of gravitational force.

A flow channel 19 is connected to the first opening 115 of the mononuclear cell collector 15. The flow channel 19 may have a structure configured to make the interior closed from the outside air. The closed space comprising the interior of the flow channel 19 can be configured such that the exchange of gas, viruses, microorganisms, impurities, and so forth, with the outside does not occur. The flow channel 19 may be inset and embedded in a gas-impermeable material. At least a portion of the flow channel 19 may be formed by inscribing in a member. At least a portion of the flow channel 19 may be formed by inscribing in a member and overlaying the recess.

A flow channel 117 is connected to the second opening 116 of the mononuclear cell collector 15. The flow channel 117 may have a structure configured to make the interior closed from the outside air. The closed space comprising the interior of the flow channel 117 may be configured such that the exchange of gas, viruses, microorganisms, impurities, and so forth, with the outside does not occur. The flow channel 117 may be inset and embedded in a gas-impermeable material. At least a portion of the flow channel 117 may be formed by inscribing in a member. At least a portion of the flow channel 117 may be formed by inscribing in a member and overlaying the recess. As shown in FIG. 1, a fluid machinery 21, e.g., a pump, for transferring fluid within the flow channel 117 is disposed in the flow channel 117.

As shown in FIG. 2, the bottom of the mononuclear cell collector 15 may be funnel shaped. In this case, for example, a first opening 115 is provided at the tip of the funnel-shaped bottom of the mononuclear cell collector 15 and a second opening 116 is provided in a side of the funnel-shaped bottom. A filter that cannot be traversed by mononuclear cells may be provided in the second opening 116.

A diluent, e.g., a buffer solution, may be held in the interior of the mononuclear cell collector 15. The diluent may be introduced via a flow channel 60 into the mononuclear cell collector 15 from a liquid diluent container 61, shown in FIG. 1, that holds liquid diluent. The liquid diluent container 61 may be capable of undergoing a change in the volume of the liquid diluent container. In addition, for example, the flow channel 19 and the flow channel 117 are filled with diluent.

At least either of the liquid diluent container 61 and the flow channel 60 may have a structure configured to make the interior closed from the outside air. The closed space comprising the interior of the liquid diluent container 61 and flow channel 60 may be configured such that the exchange of gas, viruses, microorganisms, impurities, and so forth, with the outside does not occur. The liquid diluent container 61 and flow channel 60 may be inset and embedded in a gas-impermeable material. At least a portion of the liquid diluent container 61 and flow channel 60 may be formed by inscribing in a member. At least a portion of the liquid diluent container 61 and flow channel 60 may be formed by inscribing in a member and overlaying the recess.

A flow channel 17 for transporting, from the erythrocyte removal vessel 11 to the mononuclear cell collector 15, treated blood from which erythrocytes have been at least partially removed is disposed between the erythrocyte removal vessel 11 and the mononuclear cell collector 15. The flow channel 17 can have a structure configured to make the interior closed from the outside air. The closed space comprising the interior of the flow channel 17 may be configured such that the exchange of gas, viruses, microorganisms, impurities, and so forth, with the outside does not occur. The flow channel 17 may be inset and embedded in a gas-impermeable material. At least a portion of the flow channel 17 may be formed by inscribing in a member. At least a portion of the flow channel 17 may be formed by inscribing in a member and overlaying the recess.

A flow channel 16 for transporting fluid, e.g., a gas such as air, from the mononuclear cell collector 15 to the erythrocyte removal vessel 11 is disposed between the erythrocyte removal vessel 11 and the mononuclear cell collector 15. The flow channel 16 may have a structure configured to make the interior closed from the outside air. The closed space comprising the interior of the flow channel 16 may be configured such that the exchange of gas, viruses, microorganisms, impurities, and so forth, with the outside does not occur. The flow channel 16 may be inset and embedded in a gas-impermeable material. At least a portion of the flow channel 16 may be formed by inscribing in a member. At least a portion of the flow channel 16 may be formed by inscribing in a member and overlaying the recess.

A fluid machinery 18, e.g., a pump, for transferring fluid within the flow channel 17 is disposed in the flow channel 17. A fluid machinery may be disposed in the flow channel 16, or fluid machineries may be disposed in both the flow channel 16 and the flow channel 17.

In the case where a gas and a diluent have been preliminarily filled into the mononuclear cell collector 15, when the fluid machinery 18 suctions via the flow channel 17 treated blood from which erythrocytes have been at least partially removed in the erythrocyte removal vessel 11, and supplies the suctioned treated blood from which erythrocytes have been at least partially removed into the mononuclear cell collector 15, the gas in the mononuclear cell collector 15 is pushed by the pressure and is transported via the flow channel 16 into the erythrocyte removal vessel 11. Proceeding in this manner, the pressure in the erythrocyte removal vessel 11 and the mononuclear cell collector 15 can be equilibrated by transporting the treated blood from which erythrocytes have been at least partially removed in the erythrocyte removal vessel 11 into the mononuclear cell collector 15 and transporting the gas in the mononuclear cell collector 15 into the erythrocyte removal vessel 11. Diluent may be repeatedly supplied from the liquid diluent container 61.

The fluid machinery 18 may suction, via the flow channel 17, the gas in the mononuclear cell collector 15 and may supply the suctioned gas into the erythrocyte removal vessel 11. In this case, the treated blood from which erythrocytes have been at least partially removed in the erythrocyte removal vessel 11 is pushed by pressure and is transported via the flow channel 16 into the mononuclear cell collector 15. Proceeding in this manner makes it possible to also transport the treated blood from which erythrocytes have been at least partially removed in the erythrocyte removal vessel 11 into the mononuclear cell collector 15 through the removal of the gas in the mononuclear cell collector 15.

In the case where the erythrocytes have been sedimented in the erythrocyte removal vessel 11, the supernatant in the erythrocyte removal vessel 11 is transported, as treated blood from which erythrocytes have been at least partially removed, into the mononuclear cell collector 15.

As shown in FIG. 2(*a*), the treated blood from which erythrocytes have been at least partially removed, that has been transported into the mononuclear cell collector 15 is diluted with diluent. The platelets in the diluted treated blood solution are suspended and the mononuclear cells sediment to the bottom of the mononuclear cell collector 15. The diluent may contain an erythrocyte removal agent. In this case, the erythrocytes remaining in the treated blood solution are hemolyzed.

As shown in FIG. 2(*b*), the sedimented mononuclear cells accumulate at the tip of the funnel-shaped bottom of the mononuclear cell collector 15. After the mononuclear cells in the diluted treated blood solution have sedimented, as shown in FIG. 2(*c*), the fluid machinery 21 shown in FIG. 1 and disposed in the flow channel 117 connected to the second opening 116 in the mononuclear cell collector 15, suctions the diluted treated blood solution, which is the supernatant. The suction force used to suction the supernatant is set such that the mononuclear cells sedimented as shown in FIG. 2(*c*) are not readily suctioned. The supernatant contains platelets and hemolyzed erythrocytes. The mononuclear cells can thus be separated from the platelets and erythrocytes by the suction removal of the supernatant from the mononuclear cell collector 15. The suctioned supernatant may be transported into the erythrocyte removal vessel 11 or into the blood container 10 shown in FIG. 1. In addition, gas in about the same volume as the supernatant suctioned from within the mononuclear cell collector 15 may be transported into the mononuclear cell collector 15 from within the erythrocyte removal vessel 11 or from within the blood container 10.

A mononuclear cell suction device 20, which suctions the mononuclear cells that have accumulated at the bottom of the mononuclear cell collector 15, is disposed in the flow channel 19. A fluid machinery such as a pump can be used for the mononuclear cell suction device 20. The size of the first opening 115 shown in FIG. 2 is set such that: the mononuclear cells pack the first opening 115 in the case where the mononuclear cell suction device 20 is not suctioning the mononuclear cells; the mononuclear cells can pass through the first opening 115 in the case where the mononuclear cell suction device 20 is suctioning the mononuclear cells. In the case where the mononuclear cell suction device 20 suctions the mononuclear cells, the mononuclear cells are transferred from the mononuclear cell collector 15 into the flow channel 19.

The mononuclear cells in the mononuclear cell collector 15 may be transferred into the flow channel 19 by pressurization within the mononuclear cell collector 15. In this case, the mononuclear cell suction device 20 may or may not be disposed in the flow channel 19.

As shown in FIG. 1, a cell culture device 200 according to the first embodiment comprises a cell culture vessel 22 for culturing cells. The cell culture vessel 22 may have a structure configured to make the interior closed from the outside air. The closed space comprising the interior of the cell culture vessel 22 can be configured such that the exchange of gas, viruses, microorganisms, impurities, and so forth, with the outside does not occur. The cell culture vessel 22 may be inset and embedded in a gas-impermeable material. At least a portion of the cell culture vessel 22 may be formed by inscribing in a member. At least a portion of the cell culture vessel 22 may be formed by inscribing in a member and overlaying the recess.

Cells may be adherent cultured or may be suspension cultured in the cell culture vessel 22. In the case of adherent cell culture, the interior of the cell culture vessel 22 may be coated with a cell adhesion coating agent, e.g., Matrigel™, collagen, polylysine, fibronectin, vitronectin, laminin, and so forth. The description proceeds using the example of suspension culture. The interior of the cell culture vessel 22 may be partitioned by a culture medium component-permeable member that cells cannot pass through, but which is permeable to culture medium components and waste products. In order to prevent cell adhesion, the interior wall of the cell culture vessel 22 may be coated with a cell-nonadherent material, e.g., poly-2-hydroxyethyl methacrylate (poly-HEMA) to render the inner wall of the cell culture vessel 22 nonadherent for cells. A window that enables observation of the interior may be provided in the cell culture vessel 22. For example, glass or plastic may be used as the material of the window.

A temperature control element may be disposed in the cell culture vessel 22 in order to heat and cool the window. The temperature control element may be a transparent heater, e.g., a transparent electroconductive film, that is disposed at or in the window and heats the window. Alternatively, the cell culture vessel 22 may comprise a temperature control element for heating and cooling the housing. Control of the temperature of the culture medium within the cell culture vessel 22 is made possible by controlling the temperature of the housing using the temperature control element. The cell culture vessel 22 may further comprise a thermometer that measures the temperature of the culture medium in the cell culture vessel 22. The thermometer can measure the temperature of the culture medium based on the temperature of the cell culture vessel 22 and thus without contacting the culture medium, or can be in contact with the culture medium and can directly measure the temperature of the culture medium. In this case, the temperature control element may engage in feedback control such that the temperature of the culture medium assumes a prescribed temperature. The temperature of the culture medium is controlled to, for example, 20° C. to 45° C.

The flow channel 19 is connected to the cell culture vessel 22. Cells are delivered into the cell culture vessel 22 via the flow channel 19. A flow channel 23 is connected to the flow channel 19. The flow channel 23 may have a structure configured to make the interior closed from the outside air. The closed space comprising the interior of the flow channel 23 can be configured such that the exchange of gas, viruses, microorganisms, impurities, and so forth, with the outside does not occur. The flow channel 23 may be inset and embedded in a gas-impermeable material. At least a portion of the flow channel 23 may be formed by inscribing in a member. At least a portion of the flow channel 23 may be formed by inscribing in a member and overlaying the recess. A fluid machinery 24, e.g., a pump, is disposed in the flow channel 23 in order to transfer fluid within the flow channel 23.

For example, a first culture medium container 25, which is a fluid container that holds a somatic cell culture medium, e.g., a differentiated cell culture medium, is connected to the flow channel 23. The somatic cell culture medium may be a gel or may be a liquid.

The culture medium may contain a polymer compound in the case where the culture medium is a gel form. The polymer compound may be, for example, at least one selected from the group consisting of gellan gum, deacylated gellan gum, hyaluronic acid, rhamsan gum, diutan gum, xanthan gum, carrageenan, fucoidan, pectin, pectic acid, pectinic acid, heparan sulfate, heparin, heparitin sulfate, keratin sulfate, chondroitin sulfate, dermatan sulfate, rhamnan sulfate, and salts of the preceding. The culture medium may contain methyl cellulose. Cell aggregation is well inhibited by the incorporation of methyl cellulose.

Alternatively, the culture medium may contain at least a temperature-sensitive gel selected from poly(glycerol monomethacrylate) (PGMA), poly(2-hydroxypropyl methacrylate) (PHPMA), poly(N-isopropylacrylamide) (PNIPAM), and amine-terminated, carboxylic acid-terminated, maleimide-terminated, N-hydroxysuccinimide (HNS) ester terminated, or triethoxysilane-terminated poly(N-isopropylacrylamide-co-acrylamide), poly(N-isopropylacrylamide-co-acrylic acid), poly(N-isopropylacrylamide-co-butyl acrylate), poly(N-isopropylacrylamide-co-methacrylic acid), poly(N-isopropylacrylamide-co-methacrylic acid-co-octadecyl acrylate), and N-isopropylacrylamide.

In the present disclosure, gel-form culture media and gel culture media include polymer culture media.

In the case where the cells delivered from the flow channel 19 into the cell culture vessel 22 are mononuclear cells that are somatic cells, for example, a blood cell culture medium can be used for the somatic cell culture medium. The first culture medium container 25 may have a structure configured to make the interior closed from the outside air. The closed space comprising the interior of the first culture medium container 25 may be configured such that the exchange of gas, viruses, microorganisms, impurities, and so forth, with the outside does not occur. The first culture medium container 25 may be inset and embedded in a gas-impermeable material. At least a portion of the first culture medium container 25 may be formed by inscribing in a member. At least a portion of the first culture medium container 25 may be formed by inscribing in a member and overlaying the recess. The first culture medium container 25 may be capable of undergoing a change in the volume of the first culture medium container 25. In this case, for example, the first culture medium container 25 comprises a syringe that holds a somatic cell culture medium, and a plunger inserted in the syringe and movable within the syringe; the volume within the syringe that can hold the somatic cell culture medium can be changed by moving the plunger. Alternatively, the first culture medium container 25 may be a flexible bellows or bag.

In the case where mononuclear cells are transported from the mononuclear cell collector 15 into the flow channel 19, the fluid machinery 24 delivers the somatic cell culture medium via the flow channel 23 from the first culture medium container 25 into the flow channel 19. The first culture medium container 25 reduces the volume that can hold the somatic cell culture medium. The volume of the first culture medium container 25 may be actively contracted, or the volume may be passively contracted by suction force from within the flow channel 23. The somatic cell culture medium that has been delivered into the flow channel 19 via the flow channel 23 and the mononuclear cells within the flow channel 19 are intermixed and delivered into the cell culture vessel 22.

A temperature control device that adjusts the temperature of the culture medium in the first culture medium container 25, may be disposed in or at the first culture medium container 25.

For example, a first variable-volume container 27 is connected via a flow channel 26 to the cell culture vessel 22. The flow channel 26 may have a structure configured to make the interior closed from the outside air. The closed space comprising the interior of the flow channel 26 may be configured such that the exchange of gas, viruses, microorganisms, impurities, and so forth, with the outside does not occur. The flow channel 26 may be inset and embedded in a gas-impermeable material. At least a portion of the flow channel 26 may be formed by inscribing in a member. At least a portion of the flow channel 26 may be formed by inscribing in a member and overlaying the recess. A fluid machinery 28, e.g., a pump, may be disposed in the flow channel 26 in order to transfer fluid within the flow channel 26.

The first variable-volume container 27 may have a structure configured to make the interior closed from the outside air. The closed space comprising the interior of the first variable-volume container 27 may be configured such that the exchange of gas, viruses, microorganisms, impurities, and so forth, with the outside does not occur. The first variable-volume container 27 may be inset and embedded in a gas-impermeable material. At least a portion of the first variable-volume container 27 may be formed by inscribing in a member. At least a portion of the first variable-volume container 27 may be formed by inscribing in a member and overlaying the recess. The first variable-volume container 27 may be capable of undergoing a change in the volume of the first variable-volume container 27. In this case, for example, the first variable-volume container 27 comprises a syringe that holds fluid, and a plunger inserted in the syringe and movable within the syringe; the volume within the syringe that can hold fluid can be changed by moving the plunger. Alternatively, the first variable-volume container 27 may be a flexible bellows or bag.

For example, a second variable-volume container 30 is connected via a flow channel 29 to the cell culture vessel 22. The flow channel 29 may have a structure configured to make the interior closed from the outside air. The closed space comprising the interior of the flow channel 29 may be configured such that the exchange of gas, viruses, microorganisms, impurities, and so forth, with the outside does not occur. The flow channel 29 may be inset and embedded in a gas-impermeable material. At least a portion of the flow channel 29 may be formed by inscribing in a member. At least a portion of the flow channel 29 may be formed by inscribing in a member and overlaying the recess. A fluid machinery, e.g., a pump, may be disposed in the flow channel 29 in order to transfer fluid within the flow channel 29.

The second variable-volume container 30 may have a structure configured to make the interior closed from the outside air. The closed space comprising the interior of the second variable-volume container 30 may be configured such that the exchange of gas, viruses, microorganisms, impurities, and so forth, with the outside does not occur. The second variable-volume container 30 may be inset and embedded in a gas-impermeable material. At least a portion of the second variable-volume container 30 may be formed by inscribing in a member. At least a portion of the second variable-volume container 30 may be formed by inscribing in a member and overlaying the recess. The second variable-volume container 30 may be capable of undergoing a change in the volume of the second variable-volume container 30. In this case, for example, the second variable-volume container 30 comprises a syringe that holds fluid, and a plunger inserted in the syringe and movable within the syringe; the volume within the syringe that can hold fluid can be changed by moving the plunger. Alternatively, the second variable-volume container 30 may be a flexible bellows or bag.

In the case where mononuclear cells and a somatic cell culture medium are transported from the flow channel 19 into the cell culture vessel 22, the gas, e.g., air, in the cell culture vessel 22, for example, is transferred into the second variable-volume container 30 and the second variable-volume container 30 undergoes an expansion in volume and intakes the gas that has been transferred from within the cell culture vessel 22. The volume of the second variable-volume container 30 may be actively expanded, or the volume may be passively expanded through the action of pressure.

The first variable-volume container 27, for example, holds in its interior a substance such as a factor that induces cells in a first state into cells in a second state, e.g., an induction factor. The induction factor may be RNA, protein, or a compound. The RNA may be a modified RNA or may be an unmodified RNA. The first variable-volume container 27 may contain, for example, a lipofection reagent. The induction factor may be incorporated in a plasmid vector or in a virus or viral vector, e.g., a retrovirus vector, lentivirus vector, or Sendai virus vector. In the present disclosure, induction denotes, e.g., reprogramming, initialization, transformation, transdifferentiation or lineage reprogramming, induction of differentiation, and cell fate reprogramming. Reprogramming factors include, for example, OCT3/4, SOX2, KLF4, and c-MYC. In the case where iPS cells are prepared by introducing an induction factor, e.g., a reprogramming factor, into mononuclear cells, the fluid machinery 28 transfers, via the flow channel 26, a mononuclear cell-containing somatic cell culture medium in the cell culture vessel 22 into the first variable-volume container 27. In addition, the first variable-volume container 27 undergoes a volume expansion and intakes the mononuclear cell-containing somatic cell culture medium. The volume of the first variable-volume container 27 may be actively expanded, or the volume may be passively expanded through the action of pressure. The second variable-volume container 30 holding gas undergoes a volume contraction and the gas being held is delivered into the cell culture vessel 22. The volume of the second variable-volume container 30 may be actively contracted, or the volume may be passively contracted by suction force from the interior of the cell culture vessel 22.

Through their transfer from within the cell culture vessel 22 to within the first variable-volume container 27, the mononuclear cells are brought into contact with the induction factor present in the first variable-volume container 27 and the induction factor is introduced into the mononuclear cells. The somatic cell culture medium containing mononuclear cells and induction factor may be stirred by repeated volume expansion and contraction at the first variable-volume container 27.

After the elapse of a prescribed period of time, the somatic cell culture medium containing induction factor-introduced mononuclear cells in the first variable-volume container 27, is transferred by the fluid machinery 28 via the flow channel 26 into the cell culture vessel 22. The volume of the first variable-volume container 27 contracts. In addition, the second variable-volume container 30 undergoes an expansion in volume and intakes gas from within the cell culture vessel 22.

Alternatively, in the case where iPS cells are prepared by introducing an induction factor, e.g., a reprogramming factor, into mononuclear cells, the fluid machinery 28 may transfer, via the flow channel 26, an induction factor from within the first variable-volume container 27 into the cell culture vessel 22. In this case, the first variable-volume container 27 may contract in volume and the second variable-volume container 30 may expand in volume. Through its transfer from within the first variable-volume container 27 into the cell culture vessel 22, the induction factor is brought into contact with the mononuclear cells in the cell culture vessel 22 and the induction factor is introduced into the mononuclear cells. The fluid machinery 28 may transfer the induction factors in the first variable-volume container 27 via the flow channel 26 into the cell culture vessel 22 over a plurality of divided times. This results in the introduction into the mononuclear cells of the induction factor divided into a plurality of deliveries.

For example, a second culture medium container 32, as a fluid container that holds, for example, culture medium, e.g., stem cell culture medium or somatic cell culture medium, is connected via the flow channel 31 to the cell culture vessel 22. An example in which the second culture medium container 32 holds a stem cell culture medium is described in the following. The stem cell culture medium may be a gel or may be a liquid. A differentiation culture medium, expansion culture medium, or maintenance culture medium can be used as the stem cell culture medium.

The flow channel 31 may have a structure configured to make the interior closed from the outside air. The closed space comprising the interior of the flow channel 31 may be configured such that the exchange of gas, viruses, microorganisms, impurities, and so forth, with the outside does not occur. The flow channel 31 may be inset and embedded in a gas-impermeable material. At least a portion of the flow channel 31 may be formed by inscribing in a member. At least a portion of the flow channel 31 may be formed by inscribing in a member and overlaying the recess. A fluid machinery 33, e.g., a pump, for transferring fluid within the flow channel 31 may be disposed in the flow channel 31.

The second culture medium container 32 may have a structure configured to make the interior closed from the outside air. The closed space comprising the interior of the second culture medium container 32 may be configured such that the exchange of gas, viruses, microorganisms, impurities, and so forth, with the outside does not occur. The second culture medium container 32 may be inset and embedded in a gas-impermeable material. At least a portion of the second culture medium container 32 may be formed by inscribing in a member. At least a portion of the second culture medium container 32 may be formed by inscribing in a member and overlaying the recess. The second culture medium container 32 may be capable of undergoing a change in the volume of the second culture medium container 32. In this case, for example, the second culture medium container 32 comprises a syringe that holds a fluid, and a plunger inserted in the syringe and movable within the syringe; the volume within the syringe that can hold fluid can be changed by moving the plunger. Alternatively, the second culture medium container 32 may be a flexible bellows or bag.

A temperature control device that adjusts the temperature of the culture medium in the second culture medium container 32, may be disposed in or at the second culture medium container 32.

For example, a third variable-volume container 35 is connected via a flow channel 34 to the cell culture vessel 22. The flow channel 34 may have a structure configured to make the interior closed from the outside air. The closed space comprising the interior of the flow channel 34 may be configured such that the exchange of gas, viruses, microorganisms, impurities, and so forth, with the outside does not occur. The flow channel 34 may be inset and embedded in a gas-impermeable material. At least a portion of the flow channel 34 may be formed by inscribing in a member. At least a portion of the flow channel 34 may be formed by inscribing in a member and overlaying the recess.

The third variable-volume container 35 may have a structure configured to make the interior closed from the outside air. The closed space comprising the interior of the third variable-volume container 35 may be configured such that the exchange of gas, viruses, microorganisms, impurities, and so forth, with the outside does not occur. The third variable-volume container 35 may be inset and embedded in a gas-impermeable material. At least a portion of the third variable-volume container 35 may be formed by inscribing in a member. At least a portion of the third variable-volume container 35 may be formed by inscribing in a member and overlaying the recess. The third variable-volume container 35 may be capable of undergoing a change in the volume of the third variable-volume container 35. In this case, for example, the third variable-volume container 35 comprises a syringe that holds fluid, and a plunger inserted in the syringe and movable within the syringe; the volume within the syringe that can hold fluid can be changed by moving the plunger. Alternatively, the third variable-volume container 35 may be a flexible bellows or bag.

After the elapse of a prescribed period of time after the introduction of induction factor into the mononuclear cells, the fluid machinery 33 transfers the stem cell culture medium in the second culture medium container 32 via the flow channel 31 into the cell culture vessel 22. Of compartments provided by partitioning the interior of the cell culture vessel 22 with a culture medium component-permeable member, the stem cell culture medium may be introduced into a compartment where cells are not present, but bordering a compartment where cells are present. A contraction in volume occurs at the second culture medium container 32 which has had the stem cell culture medium suctioned from its interior. The volume of the second culture medium container 32 may be actively contracted, or the volume may be passively contracted. The third variable-volume container 35 undergoes an expansion in volume and receives, via the flow channel 34, fluid within cell culture vessel 22 rendered in excess due to the inflow of the stem cell culture medium. Of compartments provided by partitioning the interior of the cell culture vessel 22 with the culture medium component-permeable member, the flow channel 34 may be connected to a compartment where cells are not present, but bordering a compartment where cells are present. The volume of the third variable-volume container 35 may be actively expanded, or the volume may be passively expanded by the action of pressure.

Alternatively, of compartments provided by partitioning the interior of the cell culture vessel 22 with the culture medium component-permeable member, the flow channel 34 may be connected to a compartment where cells are present. In this case, the excess cells in the cell culture vessel 22 may be sent out via the flow channel 34 to the third variable-volume container 35.

Among compartments provided by partitioning the interior of the cell culture vessel 22 with the culture medium component-permeable member, exchange of culture medium components and/or waste products between culture medium in compartments where cells are present and culture medium in compartments where cells are not present is carried out by, for example, osmotic pressure. For example, a semipermeable membrane, a mesh, or a hollow fiber membrane may be used as the culture component-permeable member. The semipermeable membrane includes dialysis membranes.

In the case where the culture component-permeable member is a semipermeable membrane, the molecular weight cut off of the semipermeable membrane is, for example, at least 0.1 kDa, at least 10 kDa, or at least 50 kDa. The semipermeable member is composed of, for example, cellulose ester, ethyl cellulose, cellulose esters, regenerated cellulose, polysulfone, polyacrylonitrile, polymethyl methacrylate, ethylene-vinyl alcohol copolymer, polyester-based polymer alloys, polycarbonate, polyamide, cellulose acetate, cellulose diacetate, cellulose triacetate, cuprammonium rayon, saponified cellulose, a Hemophan membrane, a phosphatidylcholine membrane, a vitamin E-coated membrane, and so forth.

In the case where the culture component-permeable member is a mesh, the mesh has pores smaller than the cells being cultured in the cell culture vessel 22. The material of the mesh may be, but not be limited to, for example, a resin or metal. The surface of the culture component-permeable member may be cell nonadherent.

In the case where the culture component-permeable member is a hollow fiber membrane, the hollow fiber membrane has pores smaller than the cells being cultured in the cell culture vessel 22. For example, cells may be cultured on the inside of the hollow fiber membrane.

While cells are cultured in the cell culture vessel 22, the fluid machinery 33 may transfer the stem cell culture medium in the second culture medium container 32 via the flow channel 31 into the cell culture vessel 22 in accordance with a prescribed timing. The third variable-volume container 35 may undergo an expansion in its volume and may receive used stem cell culture medium rendered in excess in the cell culture vessel 22 through the inflow of fresh stem cell culture medium. For example, the fluid machinery 33 may control the amount of culture medium supply, and/or may start and finish the culture medium transfer, in accordance with the state of the culture medium, the state of cell masses in the culture medium, the number of cells, the number of cell masses, the turbidity of the culture medium, and fluctuations in the pH.

Of compartments provided by partitioning the interior of the cell culture vessel 22 with the culture medium component-permeable member, a fluid machinery 37, e.g., a pump, may be connected via a flow channel 36 to compartments in which cells are present. The flow channel 36 may have a structure configured to make the interior closed from the outside air. The closed space comprising the interior of the flow channel 36 may be configured such that the exchange of gas, viruses, microorganisms, impurities, and so forth, with the outside does not occur. The flow channel 36 may be inset and embedded in a gas-impermeable material. At least a portion of the flow channel 36 may be formed by inscribing in a member. At least a portion of the flow channel 36 may be formed by inscribing in a member and overlaying the recess.

For example, in order to suppress cell aggregation, the fluid machinery 37 can circulate the culture medium between the flow channel 36 and the compartment in which cells are present, among the compartments provided by partitioning the interior of the cell culture vessel 22 with the culture medium component-permeable member. The fluid machinery 37 may induce continuous circulation of the culture medium or may induce circulation of the culture medium according at any timing. Alternatively, the fluid machinery 37 may stir the culture medium by causing back-and-forth motion of the culture medium between the flow channel 36 and the compartment in which cells are present, among the compartments provided by partitioning the interior of the cell culture vessel 22 with the culture medium component-permeable member. The fluid machinery 37 may engage in continuous stirring of the culture medium or may engage in stirring of the culture medium at any timing. For example, the fluid machinery 37 may control the amount of culture medium supply, and/or may start and finish culture medium transfer, in accordance with the state of the culture medium, the state of cell masses in the culture medium, the number of cells, the number of cell masses, the turbidity of the culture medium, and fluctuations in the pH.

Cells may be passaged or expansion cultured by suctioning the cells in the cell culture vessel 22 into the flow channel 36 and returning the cells into the cell culture vessel 22. A structure that dissociates cell masses may be present in the flow channel 36. For example, cell masses flowing in the flow channel 36 can be dissociated by the presence within the flow channel 36 of a meandering structure or a structure having a fluctuating diameter.

Of compartments provided by partitioning the interior of the cell culture vessel 22 with the culture medium component-permeable member, a fluid machinery 39, e.g., a pump, may be connected via a flow channel 38 to the compartment in which cells are not present. The flow channel 38 may have a structure configured to make the interior closed from the outside air. The closed space comprising the interior of the flow channel 38 may be configured such that the exchange of gas, viruses, microorganisms, impurities, and so forth, with the outside does not occur. The flow channel 38 may be inset and embedded in a gas-impermeable material. At least a portion of the flow channel 38 may be formed by inscribing in a member. At least a portion of the flow channel 38 may be formed by inscribing in a member and overlaying the recess.

For example, in order to increase the probability of contact by the culture medium with the culture medium component-permeable member, the fluid machinery 39 may circulate the culture medium between the flow channel 38 and the compartment not containing cells, among the compartments provided by partitioning the interior of the cell culture vessel 22 with the culture medium component-permeable member. The fluid machinery 39 may induce continuous circulation of the culture medium or may induce circulation of the culture medium at any timing. Alternatively, the fluid machinery 39 may stir the culture medium by causing back-and-forth motion of the culture medium between the flow channel 38 and the compartment in which cells are not present, among the compartments provided by partitioning the interior of the cell culture vessel 22 with the culture medium component-permeable member. The fluid machinery 39 may engage in continuous stirring of the culture medium or may engage in stirring of the culture medium at any timing. For example, the fluid machinery 39 may control the amount of culture medium supply, and/or may start and finish culture medium transfer, in accordance with the state of the culture medium, the state of cell masses in the culture medium, the number of cells, the number of cell masses, the turbidity of the culture medium, and fluctuations in the pH.

For example, iPS cells are prepared from induction factor-introduced mononuclear cells in the cell culture vessel 22 and are expansion cultured therein, and the iPS cells are then collected from within the cell culture vessel 22. The iPS cells may form cell masses (colonies) in the cell culture vessel 22.

According to in the present inventor's knowledge, since the cells can be cultured in a completely closed sealed space, carbon dioxide gas, nitrogen gas, oxygen gas, and so forth, do not have to be actively supplied into the cell culture vessel 22. The cell culture vessel 22 need not be placed in a $CO_2$ incubator as a consequence. In addition, cells, microorganisms, viruses, dust, and so forth, present outside the cell culture vessel 22 do not enter the sealed cell culture vessel 22 and as a consequence the cleanliness inside the cell culture vessel 22 is maintained. The cell culture vessel 22 need not be placed in a clean room as a result. However, the supply of, e.g., carbon dioxide gas, nitrogen gas, oxygen gas, and so forth, into the cell-containing closed system is not necessarily prohibited.

For example, since cells are cultured in a completely closed system in accordance with the cell culture device 200 according to the embodiment, the risk of cross-contamination due to cell leakage from the culture device can be reduced. In addition, for example, even if the cells are infected with a virus such as the HIV/hepatitis virus, the risk of operator infection by cell leakage can be reduced. Moreover, the risk of contamination of the culture medium in the cell culture vessel by, e.g., cells, viruses, mold, and so forth, in the air outside the cell culture vessel can be reduced. Using the cell culture vessel according to the embodiment, cells can also be cultured without the use of a $CO_2$ incubator.

Second Embodiment

Figure 3:
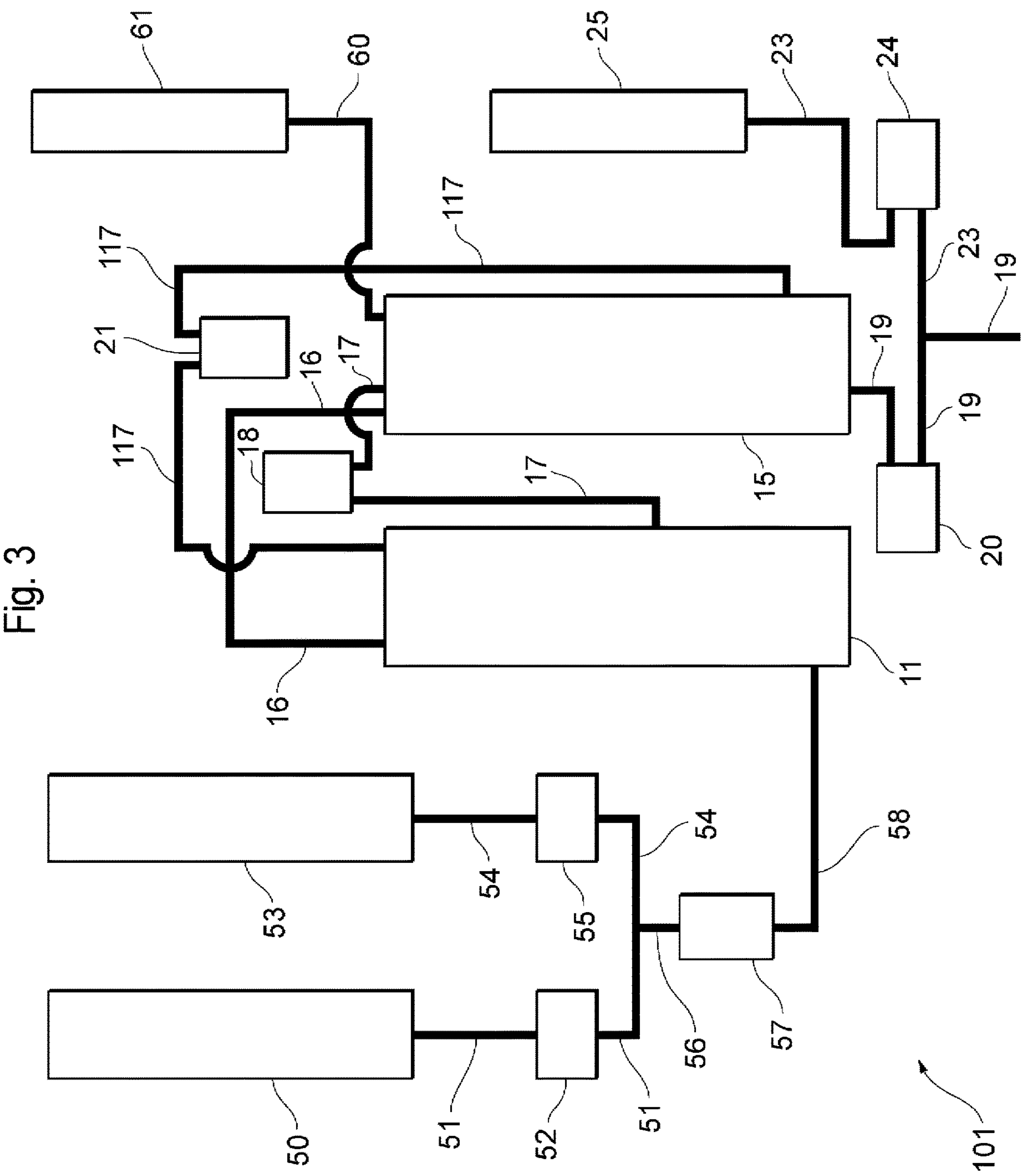
FIG. 3 is a schematic diagram of an erythrocyte removal device according to a second embodiment.

As shown in FIG. 3, an erythrocyte removal device 101 according to the second embodiment comprises a blood container 50 that holds blood and an erythrocyte treatment agent container 53 that holds an erythrocyte sedimentation agent or an erythrocyte removal agent.

The blood container 50 holds blood in its interior. The blood container 50 may have a structure configured to make the interior closed from the outside air. The closed space comprising the interior of the blood container 50 may be configured such that the exchange of gas, viruses, microorganisms, impurities, and so forth, with the outside does not occur. The blood container 50 may be inset and embedded in a gas-impermeable material. At least a portion of the blood container 50 may be formed by inscribing in a member. At least a portion of the blood container 50 may be formed by inscribing in a member and overlaying the recess. The blood container 50 may be capable of undergoing a change in the volume of the blood container 50. In this case, for example, the blood container 50 comprises a syringe that holds fluid, and a plunger inserted in the syringe and movable within the syringe; the volume within the syringe that can hold fluid can be changed by moving the plunger. Alternatively, the blood container 50 may be a flexible bellows or bag.

The erythrocyte treatment agent container 53 holds an erythrocyte sedimentation agent or an erythrocyte removal agent in its interior. The erythrocyte treatment agent container 53 may have a structure configured to make the interior closed from the outside air. The closed space comprising the interior of the erythrocyte treatment agent container 53 may be configured such that the exchange of gas, viruses, microorganisms, impurities, and so forth, with the outside does not occur. The erythrocyte treatment agent container 53 may be inset and embedded in a gas-impermeable material. At least a portion of the erythrocyte treatment agent container 53 may be formed by inscribing in a member. At least a portion of the erythrocyte treatment agent container 53 may be formed by inscribing in a member and overlaying the recess. The erythrocyte treatment agent container 53 may be capable of undergoing a change in the volume of the erythrocyte treatment agent container 53. In this case, for example, the erythrocyte treatment agent container 53 comprises a syringe that holds fluid, and a plunger inserted in the syringe and movable within the syringe; the volume within the syringe that can hold fluid can be changed by moving the plunger. Alternatively, the erythrocyte treatment agent container 53 may be a flexible bellows or bag.

The erythrocyte removal device 101 according to the second embodiment, for example, further comprises a mixer 57 that mixes blood with erythrocyte sedimentation agent or erythrocyte removal agent. The mixer 57 comprises, for example, a bent flow channel that carries a mixture of blood and erythrocyte sedimentation agent or erythrocyte removal agent. The bent flow channel may be bent in a spiral shape. A meandering flow channel may be present in the bent flow channel. The cross-sectional area in the bent flow channel may undergo repeated fluctuations. The mixer 57 may have a structure configured to make the interior closed from the outside air. The closed space comprising the interior of the mixer 57 may be configured such that the exchange of gas, viruses, microorganisms, impurities, and so forth, with the outside does not occur. The mixer 57 may be inset and embedded in a gas-impermeable material. At least a portion of the mixer 57 may be formed by inscribing in a member. At least a portion of the mixer 57 may be formed by inscribing in a member and overlaying the recess.

A flow channel 51, for transporting at least blood from the blood container 50 to the mixer 57, is connected to the blood container 50. A flow channel 54, for transporting at least erythrocyte sedimentation agent or erythrocyte removal agent from the erythrocyte treatment agent container 53 to the mixer 57, is connected to the erythrocyte treatment agent container 53. The flow channel 51 and the flow channel 54 combine into the flow channel 56. The flow channel 56 is connected to the mixer 57. A flow channel 58 for transporting the mixture of blood with erythrocyte sedimentation agent or erythrocyte removal agent mixed in the mixer 57 into the erythrocyte removal vessel 11 is connected to the mixer 57.

A fluid machinery 52, e.g., a pump, for transferring fluid in the flow channel 51, may be disposed in the flow channel 51. A fluid machinery 55, e.g., a pump, for transferring fluid in the flow channel 54, may be disposed in the flow channel 54.

The flow channels 51, 54, 56, and 58 may each have a structure configured to make the interior closed from the outside air. The closed space comprising the interior of each of the flow channels 51, 54, 56, and 58 may be configured such that the exchange of gas, viruses, microorganisms, impurities, and so forth, with the outside does not occur. The flow channels 51, 54, 56, and 58 may each be inset and embedded in a gas-impermeable material. For each of the flow channels 51, 54, 56, and 58, at least a portion may be formed by inscribing in a member. For each of the flow channels 51, 54, 56, and 58, at least a portion may be formed by inscribing in a member and overlaying the recess.

In the case where the mixture of blood and erythrocyte sedimentation agent or erythrocyte removal agent is transferred to the erythrocyte removal vessel 11, the fluid machinery 52 transfers the blood within the blood container 50 via the flow channels 51, 56 into the mixer 57. In addition, the fluid machinery 55 transfers the erythrocyte sedimentation agent or erythrocyte removal agent in the erythrocyte treatment agent container 53 via flow channels 54, 56 into the mixer 57. Otherwise, fluid machineries may not be disposed in the flow channels 51, 54, while a fluid machinery may be disposed in the flow channel 56 and the fluid machinery disposed in the flow channel 56 may transfer, to the mixer 57, the blood in the blood container 50 and the erythrocyte sedimentation agent or erythrocyte removal agent in the erythrocyte treatment agent container 53. The blood and erythrocyte sedimentation agent or erythrocyte removal agent are intermixed in the mixer 57. The mixture of blood with erythrocyte sedimentation agent or erythrocyte removal agent mixed in the mixer 57 is transferred via the flow channel 58 to the erythrocyte removal vessel 11. The erythrocyte sedimentation or hemolysis in the erythrocyte removal vessel 11 is the same as in the first embodiment. The other constituent elements of the erythrocyte removal device 101 according to the second embodiment may be the same as in the erythrocyte removal device 100 according to the second embodiment.

Third Embodiment

Figure 4:
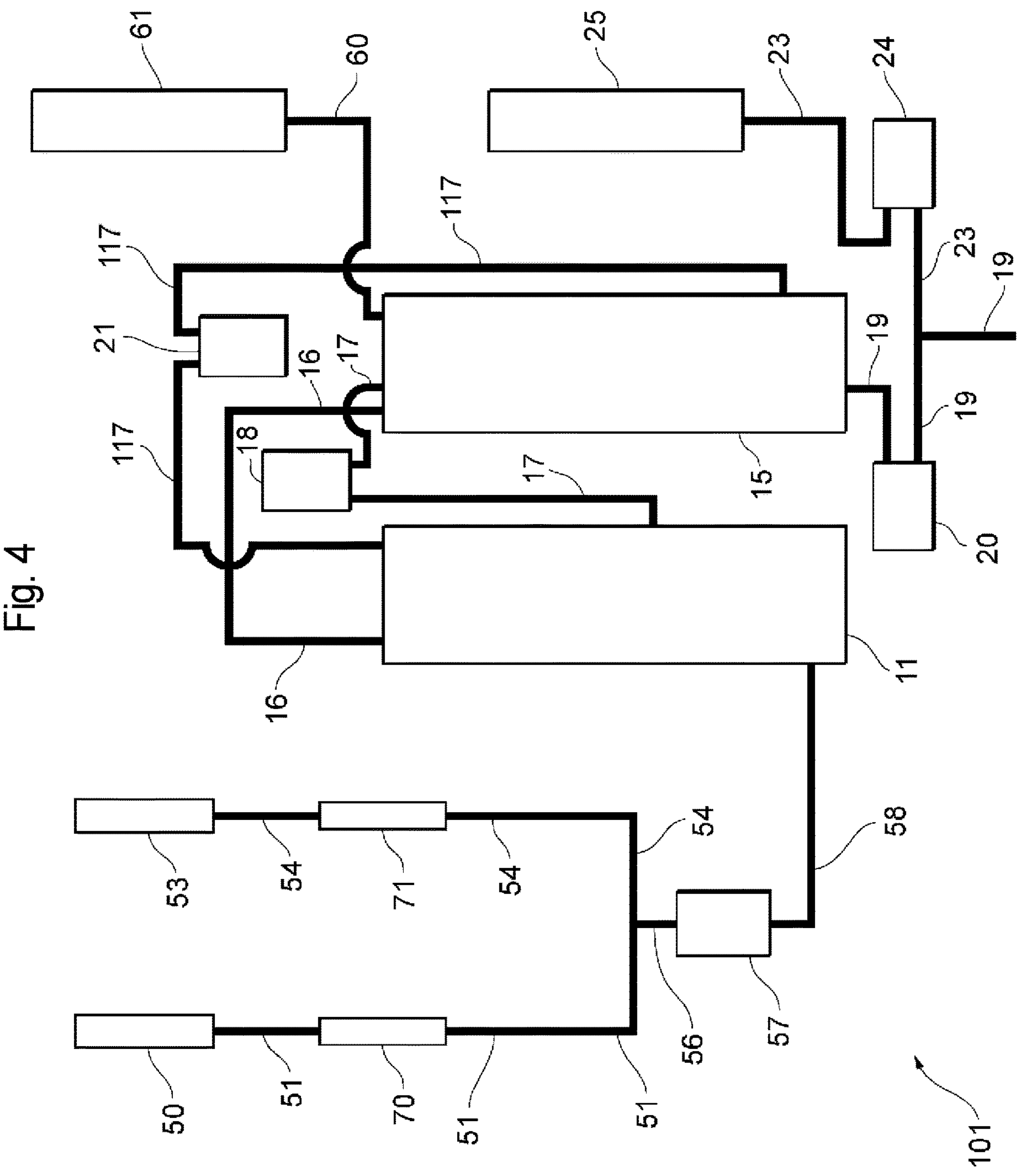
FIG. 4 is a schematic diagram of an erythrocyte removal device according to a third embodiment.

As shown in FIG. 4, the erythrocyte removal device 101 according to the third embodiment comprises a vacuum container 70, the interior of which can be placed under a vacuum, and which is disposed in the flow channel 51 for transferring at least blood from the blood container 50 to the mixer 57.

The vacuum container 70 may have a structure configured to make the interior closed from the outside air. The closed space comprising the interior of the vacuum container 70 may be configured such that the exchange of gas, viruses, microorganisms, impurities, and so forth, with the outside does not occur. The vacuum container 70 may be inset and embedded in a gas-impermeable material. At least a portion of the vacuum container 70 may be formed by inscribing in a member. At least a portion of the vacuum container 70 may be formed by inscribing in a member and overlaying the recess. The vacuum container 70 may be capable of undergoing a change in the volume of the vacuum container 70. The vacuum container 70 may be a flexible bellows or bag.

The erythrocyte removal device 101 according to the third embodiment comprises a vacuum container 71, the interior of which can be placed under a vacuum, and which is disposed in the flow channel 54 for transferring at least erythrocyte sedimentation agent or erythrocyte removal agent from the erythrocyte treatment agent container 53 to the mixer 57.

The vacuum container 71 may have a structure configured to make the interior closed from the outside air. The closed space comprising the interior of the vacuum container 71 may be configured such that the exchange of gas, viruses, microorganisms, impurities, and so forth, with the outside does not occur. The vacuum container 71 may be inset and embedded in a gas-impermeable material. At least a portion of the vacuum container 71 may be formed by inscribing in a member. At least a portion of the vacuum container 71 may be formed by inscribing in a member and overlaying the recess. The vacuum container 71 may be capable of undergoing a change in the volume of the vacuum container 71. The vacuum container 71 may be a flexible bellows or bag.

In the case where the blood container 50 is connected to the flow channel 51 with the interior of the vacuum container 70 having been preliminarily placed under a vacuum, the blood in the blood container 50 is transferred into the vacuum container 70 and the blood is further transferred into the mixer 57 via the flow channels 51, 56. In addition, in the case where the erythrocyte treatment agent container 53 is connected to the flow channel 54 with the interior of the vacuum container 71 having been preliminarily placed under a vacuum, the erythrocyte sedimentation agent or erythrocyte removal agent in the erythrocyte treatment agent container 53 is transferred into the vacuum container 71 and the blood is further transferred into the mixer 57 via the flow channels 54, 56.

The other constituent elements of the erythrocyte removal device 101 according to the third embodiment may be the same as in the second embodiment.

Fourth Embodiment

The vacuum containers 70, 71 shown in FIG. 4 may be omitted and the erythrocyte removal vessel 11 may be preliminarily brought to a vacuum. In the case where, with the erythrocyte removal vessel 11 having been preliminarily brought to a vacuum, the blood container 50 is connected to the flow channel 51 and the erythrocyte treatment agent container 53 is connected to the flow channel 54, the blood in the blood container 50 is transferred via the flow channels 51, 56 into the mixer 57 and the erythrocyte sedimentation agent or erythrocyte removal agent in the erythrocyte treatment agent container 53 is transferred into the mixer 57 via the flow channels 54, 56. Moreover, the blood and erythrocyte sedimentation agent or erythrocyte removal agent mixed in the mixer 57 are transferred into the erythrocyte removal vessel 11 via the flow channel 58.

Alternatively, in the case where the flow channel 51 and the flow channel 54 are closed with, e.g., valves, the interior of the erythrocyte removal vessel 11 is placed under a vacuum, and the valves in the flow channel 51 and the flow channel 54 are opened, the blood in the blood container 50 is transferred via the flow channels 51, 56 into the mixer 57 and the erythrocyte sedimentation agent or erythrocyte removal agent in the erythrocyte treatment agent container 53 is transferred via the flow channels 54, 56 into the mixer 57. Moreover, the blood and erythrocyte sedimentation agent or erythrocyte removal agent mixed in the mixer 57 are transferred into the erythrocyte removal vessel 11 via the flow channel 58.

Other Embodiments

The present invention has been described in the preceding using embodiments, but the description and figures making up this portion of the disclosure should not be understood as limitations on this invention. Various alternative embodiments, embodiments, and operational technologies should be clear to the individual skilled in the art based on the present disclosure. For example, the cells transported to the cell culture vessel 22 shown in FIG. 1 are not limited to mononuclear cells. The cells transported to the cell culture vessel 22 may be stem cells, fibroblasts, or other somatic cells. Any cells may be transported to the cell culture vessel 22.

The example of the preparation of iPS cells from mononuclear cells in the cell culture vessel 22 has been described in the first embodiment, but differentiated cells, e.g., nerve cells and so forth, may be prepared from stem cells in the cell culture vessel 22. The stem cells may be, for example, iPS cells, embryonic stem cells (ES cells), somatic stem cells, or other artificially induced stem cells. In this case, for example, the first variable-volume container 27 holds a differentiation-inducing factor in its interior. The present invention should be understood as encompassing, inter alia, various embodiments such as these.

EXAMPLES

Example 1

The present example shows an example of the ability to carry out cell culture in a completely closed environment, without performing culture medium exchange and without performing gas exchange. A gel culture medium was prepared by adding growth factors to a culture medium (StemSpan H3000, registered trademark, STEMCELL Technologies Inc.) and also adding deacylated gellan gum to the culture medium.

The prepared gel culture medium was introduced into a 15-mL tube and $2\times10^5$ blood cells were seeded to the gel culture medium. The 15-mL tube was then placed in a $CO_2$ incubator and the blood cells (mononuclear cells) were cultured for 7 days. A Sendai virus vector loaded with OCT3/4, SOX2, KLF4, and cMYC was then added to the gel culture medium to provide a multiplicity of infection (MOI) of 10.0 in order to infect the blood cells with the Sendai virus.

After the addition of the Sendai virus to the gel culture medium, 15 mL of gelled stem cell culture medium (DMEM/F12 containing 20% KnockOut SR (registered trademark, Thermo Fisher Scientific Inc.)) was added to the gel culture medium; this was followed by the introduction of 15 mL of the culture medium containing the Sendai virus-infected cells into a sealable cell culture vessel and injection of the gel culture medium into the cell culture vessel. The interior of the cell culture vessel was then sealed such that gas exchange between the interior of the cell culture vessel and the exterior was completely prevented.

Suspension culture of the initialization factor-transduced cells within the cell culture vessel was started. 2 mL of the gel culture medium in a culture medium holding tank 40 was exchanged for 2 mL of fresh gel culture medium once every two days.

Figure 5:
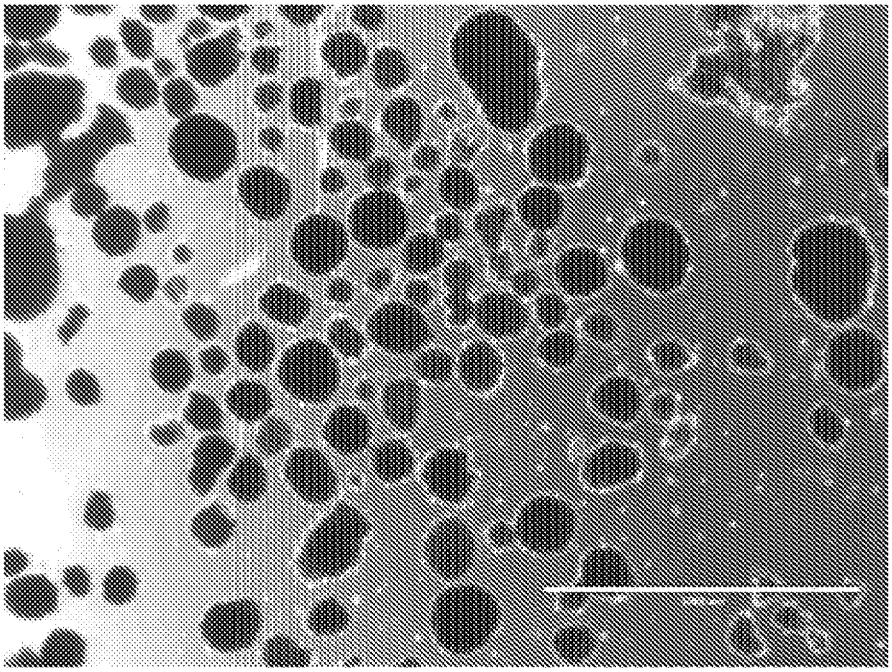
FIG. 5 is a micrograph of cell masses according to Example 1.
Figure 6:
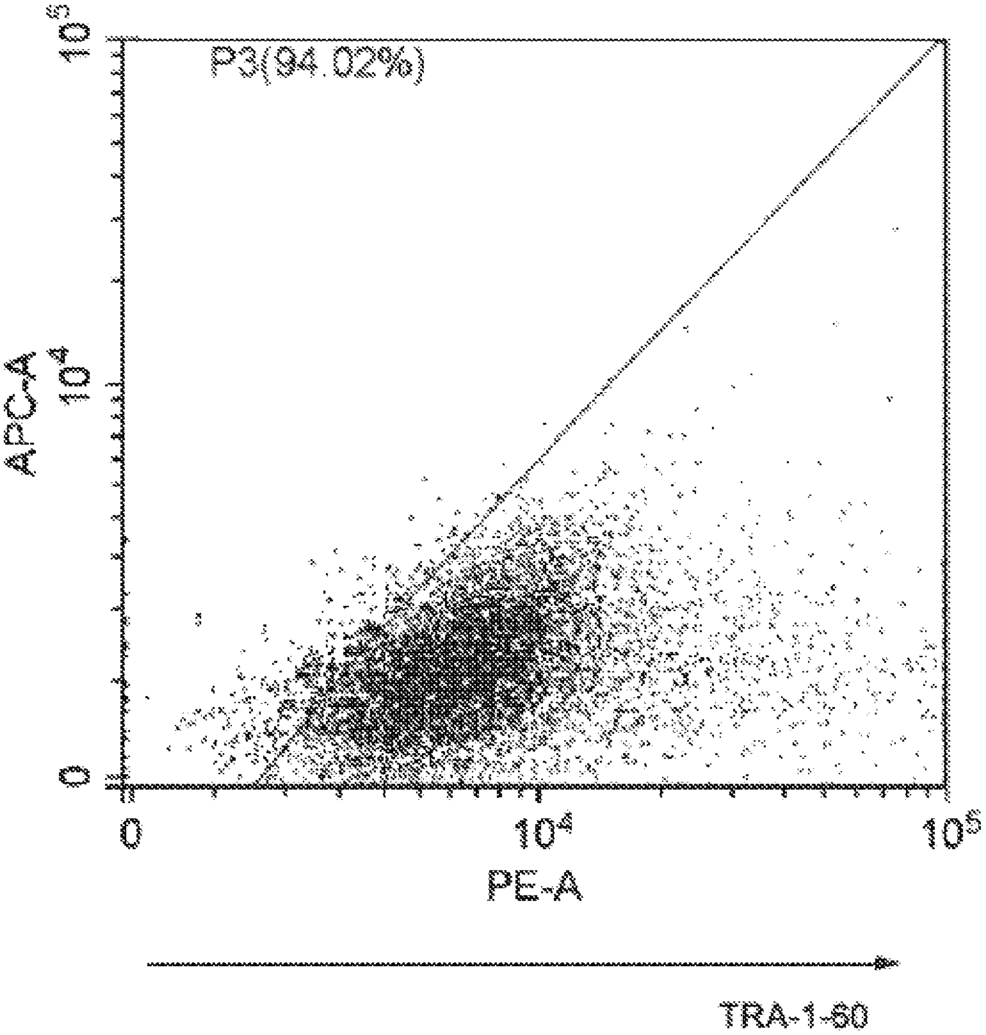
FIG. 6 is a histogram that shows the results for flow cytometry on iPS cells according to Example 1.

After 15 days, the cells were submitted to observation with a microscope, and the formation of ES cell-like colonies was confirmed, as shown in FIG. 5. In addition, the cells were fixed using 4% paraformaldehyde and the expression level of TRA-1-60 cell surface antigen in the fixed cells was measured using a flow cytometer; as shown in FIG. 6, TRA-1-60 positive was at least 90% and it was confirmed that almost complete reprogramming had occurred. Accordingly, it was shown that iPS cells could be induced from somatic cells other than stem cells in a completely closed environment without culture medium exchange and without gas exchange.

Example 2

Figure 7:
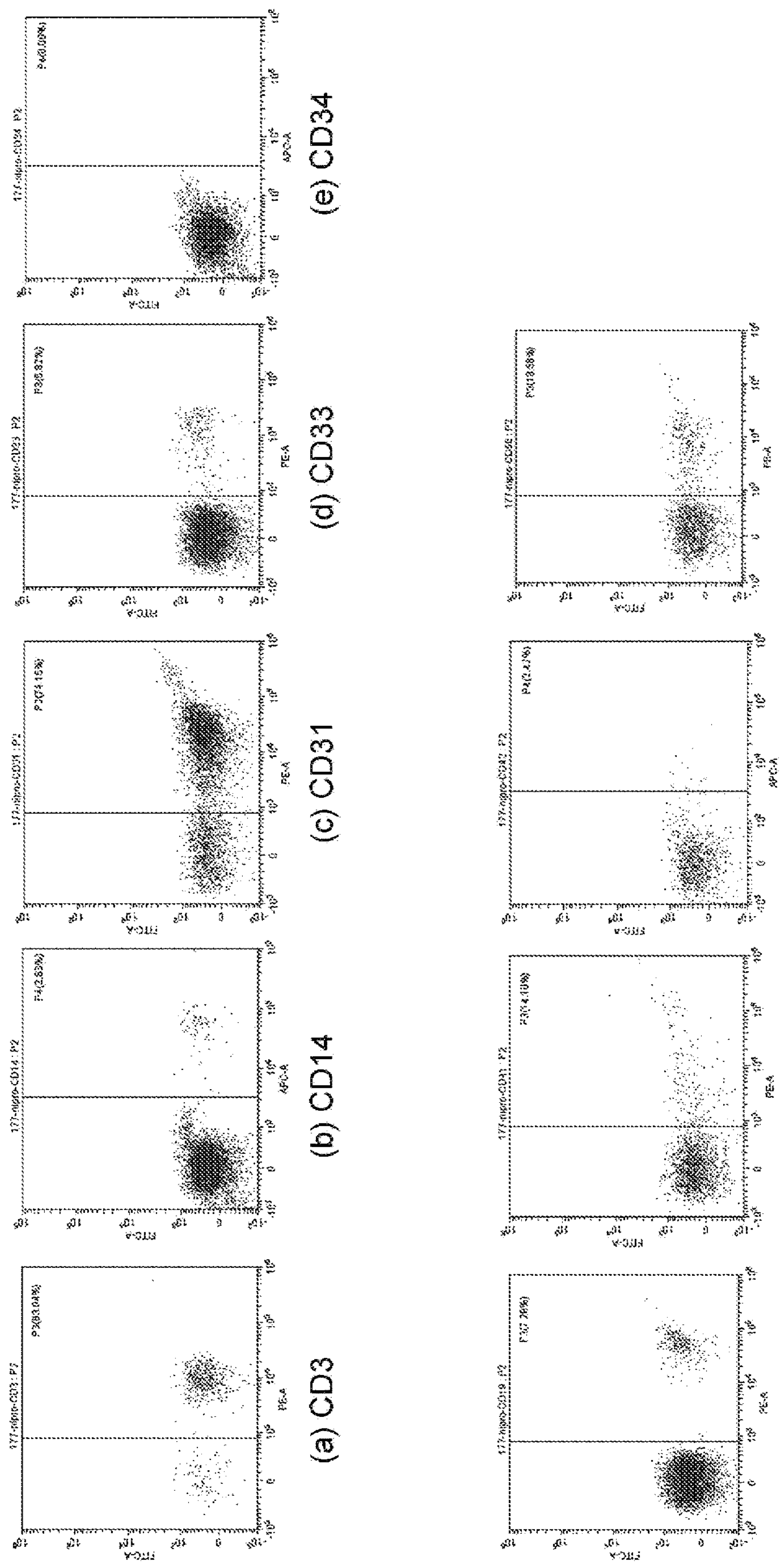
FIG. 7 shows the results of fluorescence-activated cell sorting analysis according to Example 2.

Blood was treated with an erythrocyte sedimentation agent to provide treated blood from which erythrocytes had been at least partially removed. The treated blood was treated with cell surface marker antibodies, and the results of analysis by fluorescence-activated cell sorting (FACS) are given in FIG. 7. The treated blood contained CD3-positive cells, CD14-positive cells, CD31-positive cells, CD33-positive cells, CD34-positive cells, CD19-positive cells, CD41-positive cells, CD42-positive cells, and CD56-positive cells.

Figure 8:
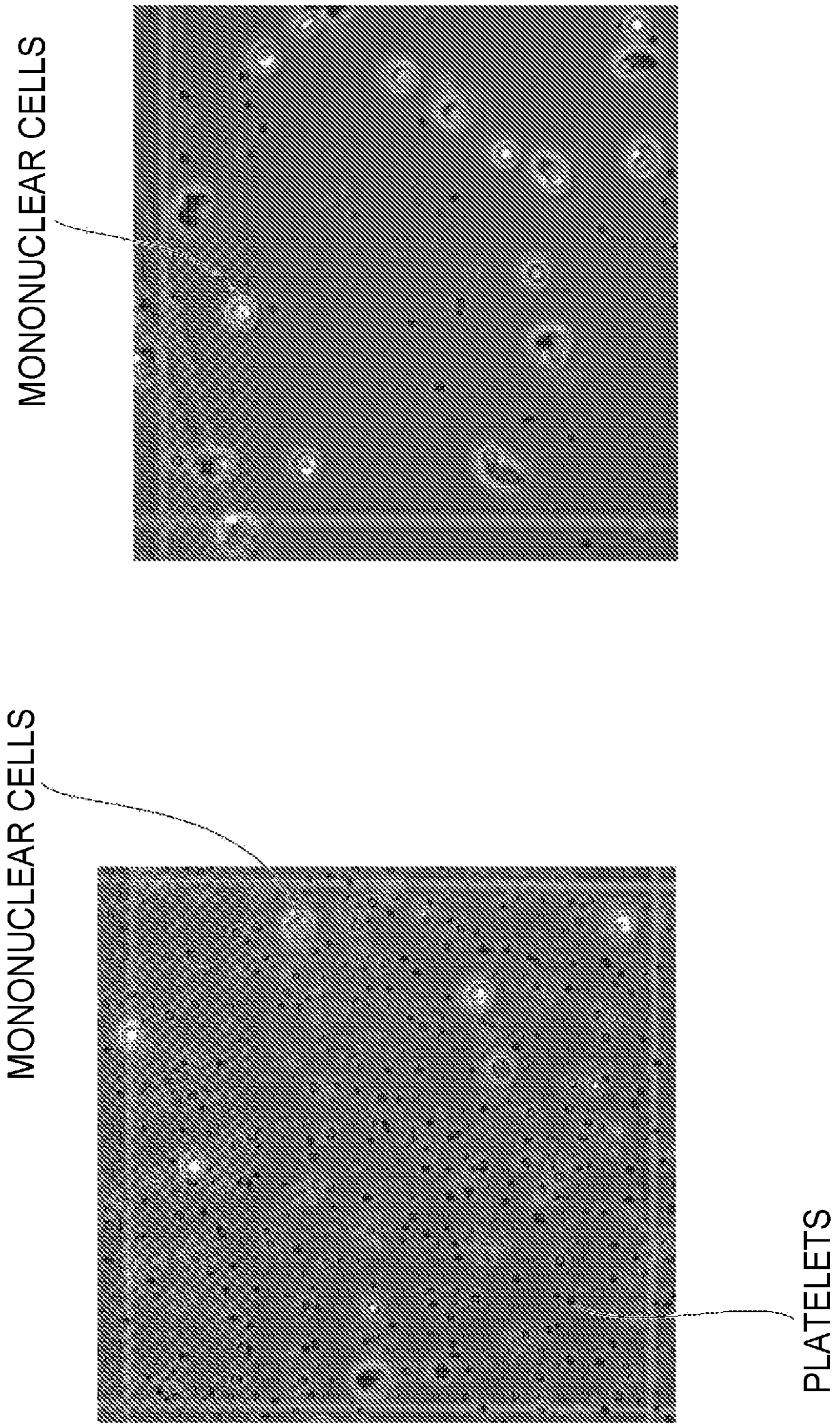
FIG. 8 shows a micrograph (a) of treated blood prior to its introduction into the mononuclear cell collector according to Example 2, and a micrograph (b) of the mononuclear cell-containing solution collected from the mononuclear cell collector.
Figure 9:
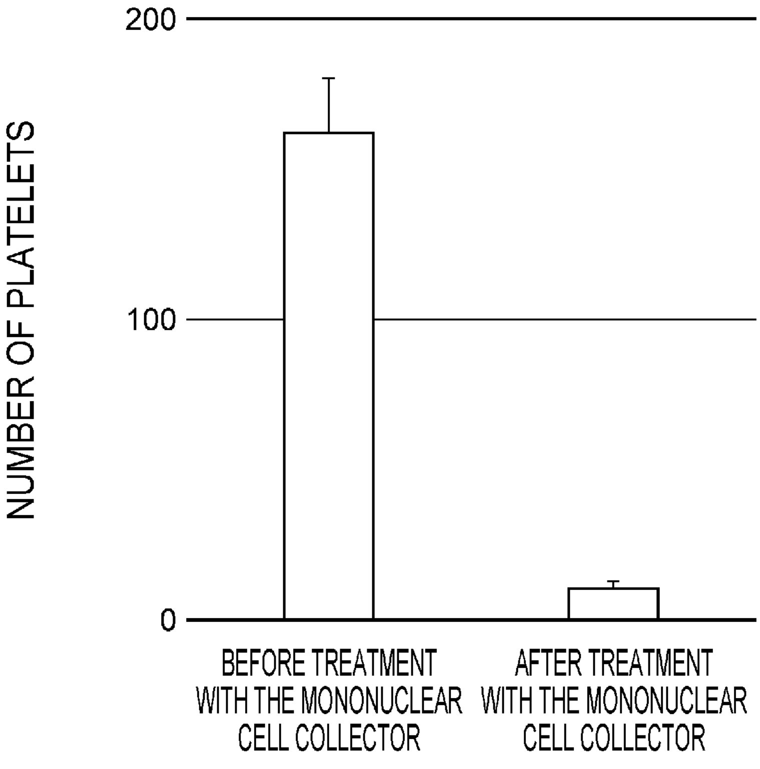
FIG. 9 is a graph that shows the number of platelets in treated blood prior to its introduction into the mononuclear cell collector according to Example 2, and the number of platelets in the mononuclear cell-containing solution collected from the mononuclear cell collector.

The treated blood from which erythrocytes have been at least partially removed was introduced into a mononuclear cell collector as shown in FIG. 2 and was diluted with buffer solution and the supernatant was removed. The mononuclear cells were then collected from the mononuclear cell collector. As shown in FIG. 8(*a*), prior to its introduction into the mononuclear cell collector, the treated blood contained numerous platelets. On the other hand, as shown in FIG. 8(*b*), the platelets had been almost completely removed from the mononuclear cell-containing solution collected from the mononuclear cell collector. FIG. 9 shows a graph that shows, for the same area, the number of platelets in the treated blood prior to its introduction into the mononuclear cell collector and the number of platelets in the mononuclear cell-containing solution collected from the mononuclear cell collector.

Figure 10:
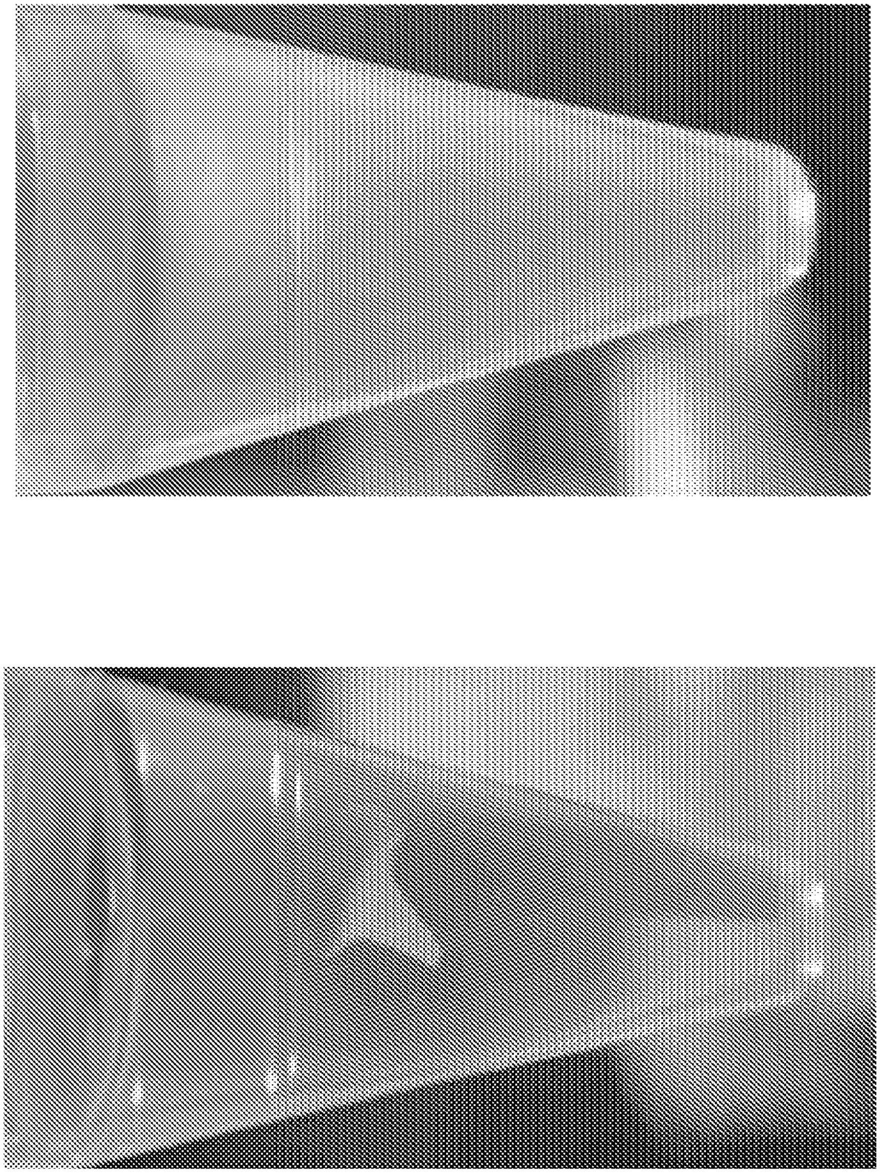
FIG. 10 shows a photograph (a) of culture medium into which platelet-containing treated blood was added prior to its introduction into the mononuclear cell collector according to Example 2, and a photograph (b) of culture medium into which the mononuclear cell-containing solution from which the platelets have been removed was added.

As shown in FIG. 10(*a*), when the platelet-containing treated blood prior to its introduction into the mononuclear cell collector was introduced into culture medium, aggregation occurred. In contrast to this, as shown in FIG. 10(*b*), when the mononuclear cell-containing solution from which the platelets had been removed was introduced into culture medium, aggregation did not occur.

Example 3

A gel culture medium was prepared by adding deacylated gellan gum to a blood culture medium. The prepared gel culture medium was introduced into a laminin-coated 6-well dish, and $2\times10^5$ blood cells (mononuclear cells) were seeded. The 6-well dish was then placed in a 37° C. $CO_2$ incubator and the blood cells were cultured for 7 days. After this, a Sendai virus vector loaded with OCT3/4, SOX2, KLF4, and cMYC (CytoTune-iPS 2.0, Thermo Fisher Scientific Inc.) was added to the blood growth culture medium to provide a multiplicity of infection (MOI) of 5 and the blood cells were infected with the Sendai virus.

Two days after the addition of the Sendai virus to the blood growth culture medium while maintaining the cells in the 6-well dish, culture medium exchange was performed using 500 μL stem cell culture medium (DMEM/F12 containing 20% KnockOut SR (registered trademark, Thermo Fisher Scientific Inc.)) or StemFit.

Figure 11:
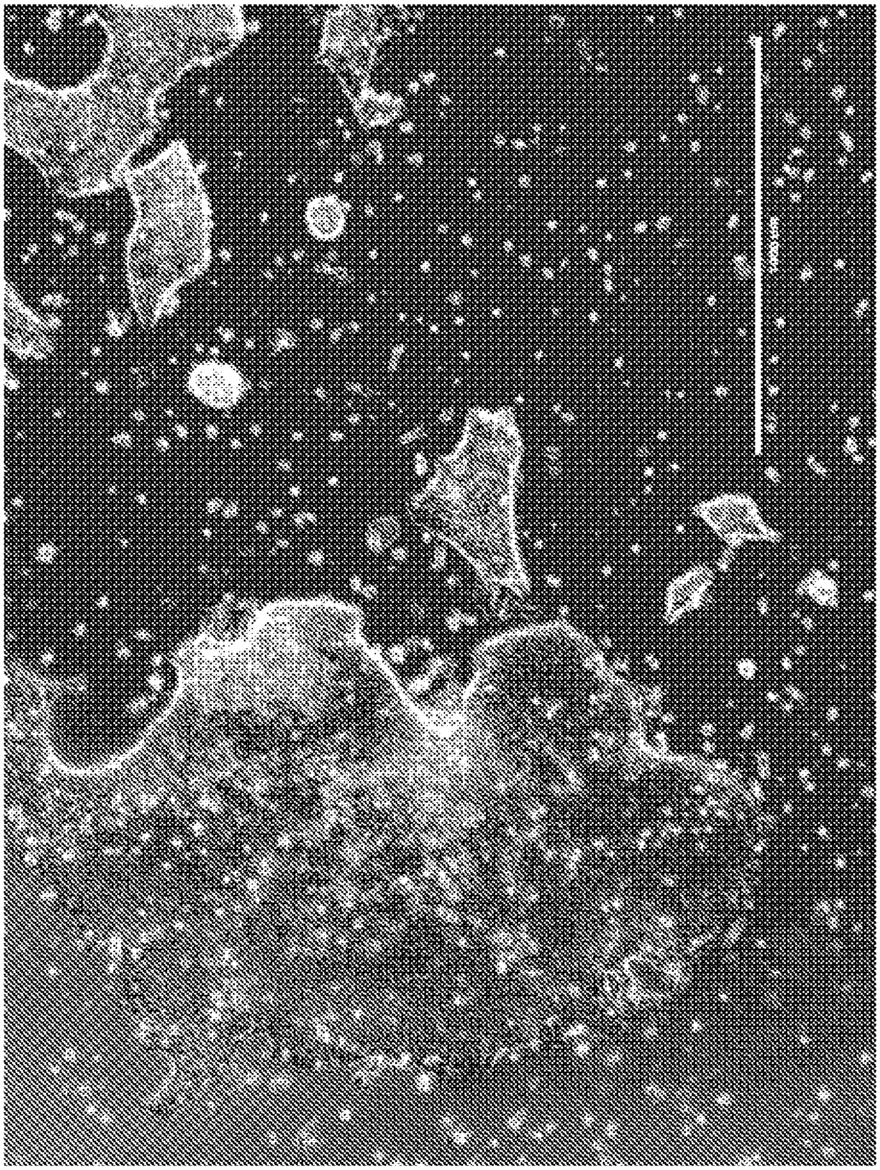
FIG. 11 is a micrograph of cells produced by the iPS cell production method according to Example 3.
Figure 12:
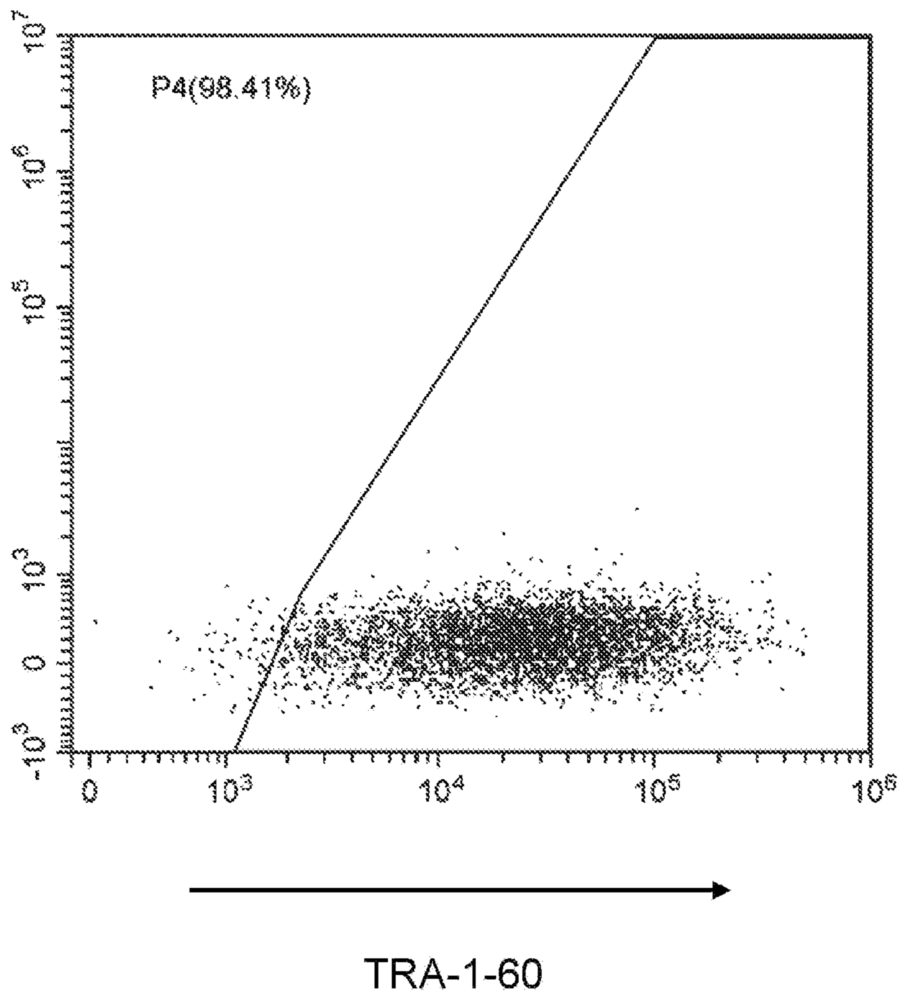
FIG. 12 is a histogram that shows the results of flow cytometric analysis of cells produced by the iPS cell production method according to Example 3.

Fifteen days after the addition of the Sendai virus to the blood growth culture medium, the cells were submitted to observation with a microscope, and the formation of ES cell-like colonies was confirmed as shown in FIG. 11. In addition, the cells were fixed using 4% paraformaldehyde and the expression level of TRA-1-60 cell surface antigen in the fixed cells was measured using a flow cytometer; as shown in FIG. 12, the post-induction cells were approximately 100% TRA-1-60 positive and it was confirmed that almost complete reprogramming had occurred. It was thus shown that cells could be reprogrammed by introducing reprogramming factors into the cells in the cell culture vessel and culturing the reprogramming factor-transduced cells in the same cell culture vessel.

Example 4

A gel culture medium was prepared by adding deacylated gellan gum to a blood culture medium. The prepared gel culture medium was introduced into a laminin-coated flask, and $5\times10^5$ blood cells (mononuclear cells) were seeded. This was followed by introduction into a 37° C. $CO_2$ incubator, and the blood cells were cultured for 7 days. After this, a Sendai virus vector loaded with OCT3/4, SOX2, KLF4, and cMYC (CytoTune-iPS 2.0, Thermo Fisher Scientific Inc.) was added to the blood growth culture medium to provide a multiplicity of infection (MOI) of 5 and the blood cells were infected with the Sendai virus.

Two days after the addition of the Sendai virus to the blood growth culture medium, the flask was completely filled with stem cell culture medium (DMEM/F12 containing 20% KnockOut SR (registered trademark, Thermo Fisher Scientific Inc.)) or StemFit so air did not remain in the flask; the flask was closed with a cap to prevent gas exchange with the outside; and the interior of the flask was closed off to prevent the permeation of cells, microorganisms, impurities, and so forth.

Figure 13:
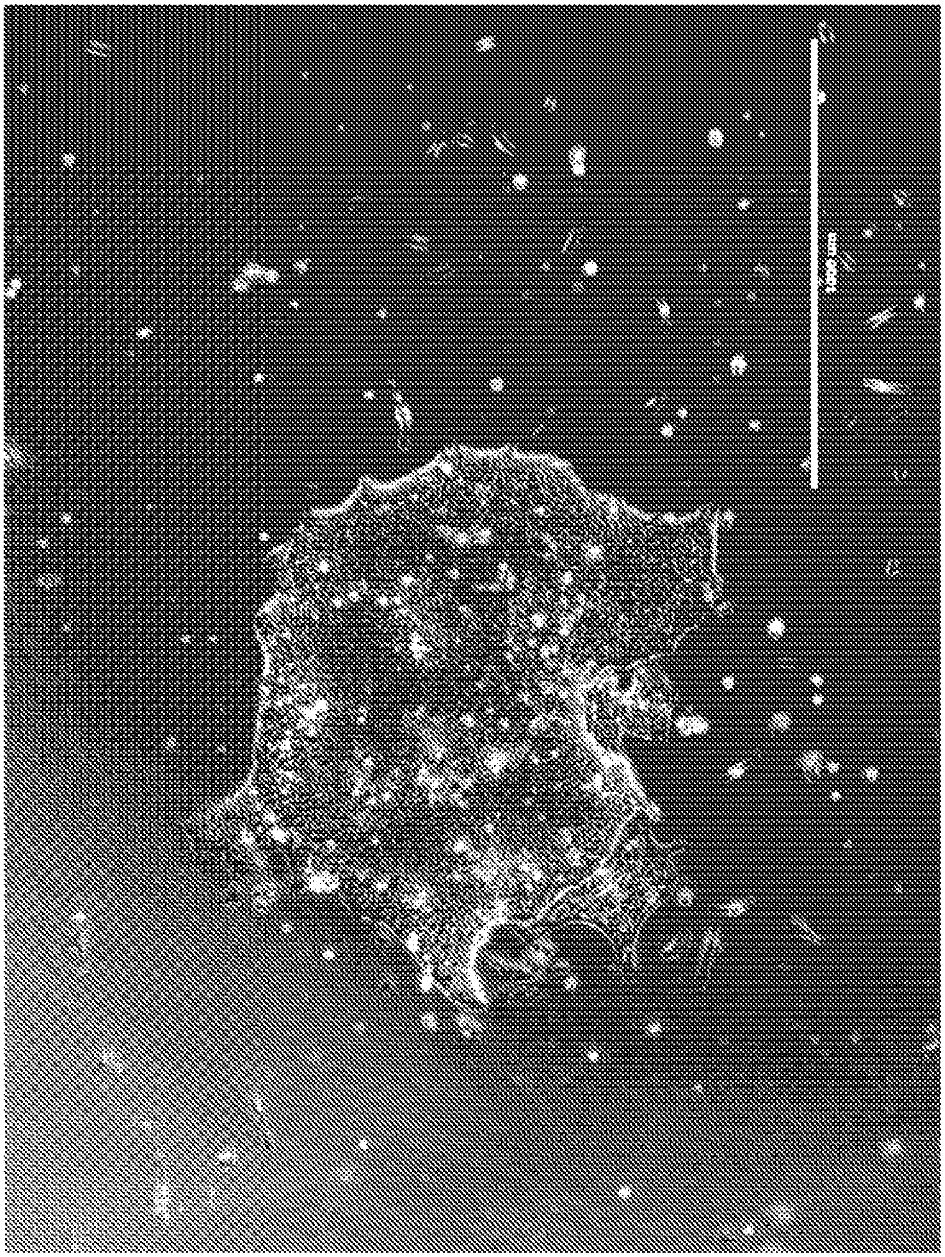
FIG. 13 is a micrograph of cells produced by the iPS cell production method according to Example 4.
Figure 14:
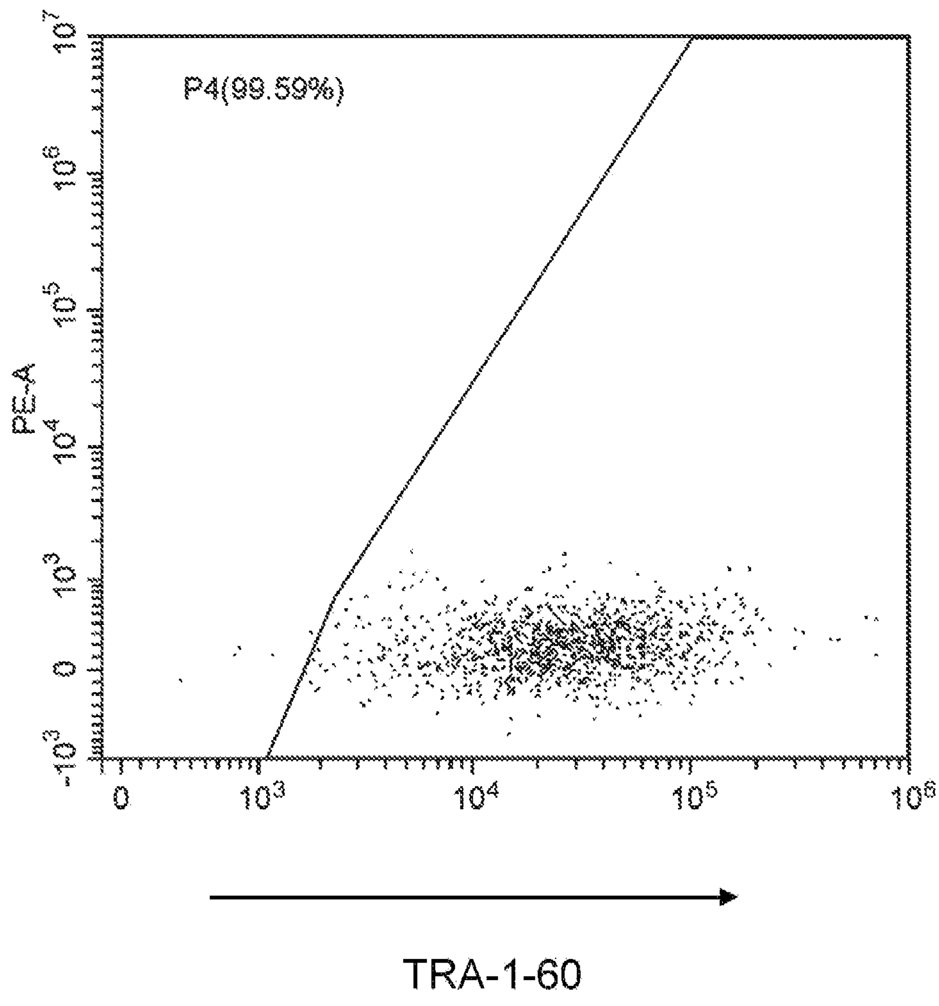
FIG. 14 is a histogram that shows the results of flow cytometric analysis of cells produced by the iPS cell production method according to Example 4.

Fifteen days after the addition of the Sendai virus to the blood growth culture medium, the cells were submitted to observation with a microscope, and the formation of ES cell-like colonies was confirmed as shown in FIG. 13. In addition, the cells were fixed using 4% paraformaldehyde and the expression level of TRA-1-60 cell surface antigen in the fixed cells was measured using a flow cytometer; as shown in FIG. 14, the post-induction cells were approximately 100% TRA-1-60 positive and it was confirmed that almost complete reprogramming had occurred. It was thus shown that cells could be reprogrammed by introducing reprogramming factors into cells in the cell culture vessel and culturing the reprogramming factor-transduced cells in the same closed cell culture vessel.

Example 5

A liquid blood growth culture medium that was not a gel was introduced into a laminin-coated 6-well dish, and $2\times10^5$ blood cells (mononuclear cells) were seeded. The 6-well dish was then placed in a 37° C. $CO_2$ incubator and the blood cells were cultured for 7 days. After this, a Sendai virus vector loaded with OCT3/4, SOX2, KLF4, and cMYC (CytoTune-iPS 2.0, Thermo Fisher Scientific Inc.) was added to the blood growth culture medium to provide a multiplicity of infection (MOI) of 5 and the blood cells were infected with the Sendai virus.

Two days after the addition of the Sendai virus to the blood growth culture medium while maintaining the cells in the 6-well dish, culture medium exchange was performed using 500 μL stem cell culture medium (DMEM/F12 containing 20% KnockOut SR (registered trademark, Thermo Fisher Scientific Inc.)) or StemFit.

Figure 15:
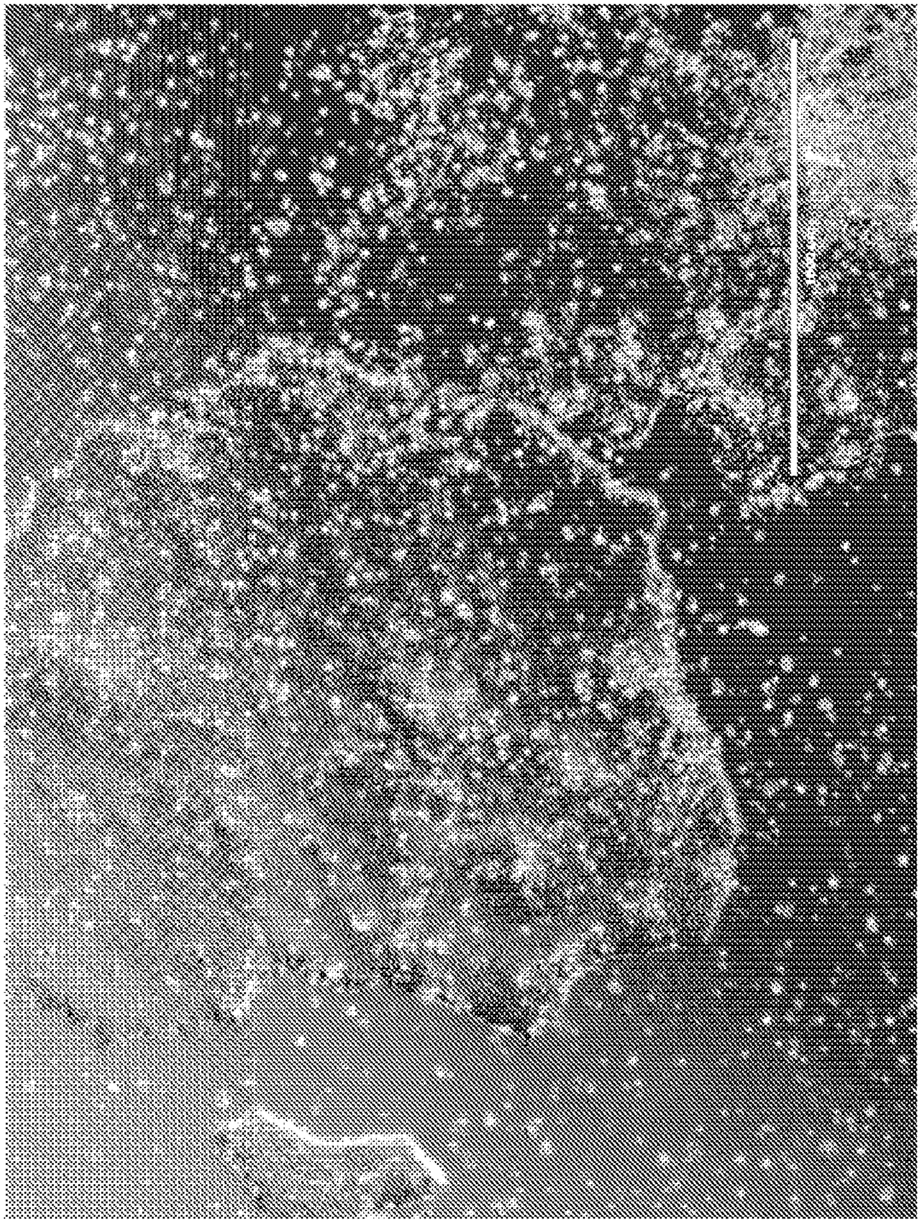
FIG. 15 is a micrograph of cells produced by the iPS cell production method according to Example 5.
Figure 16:
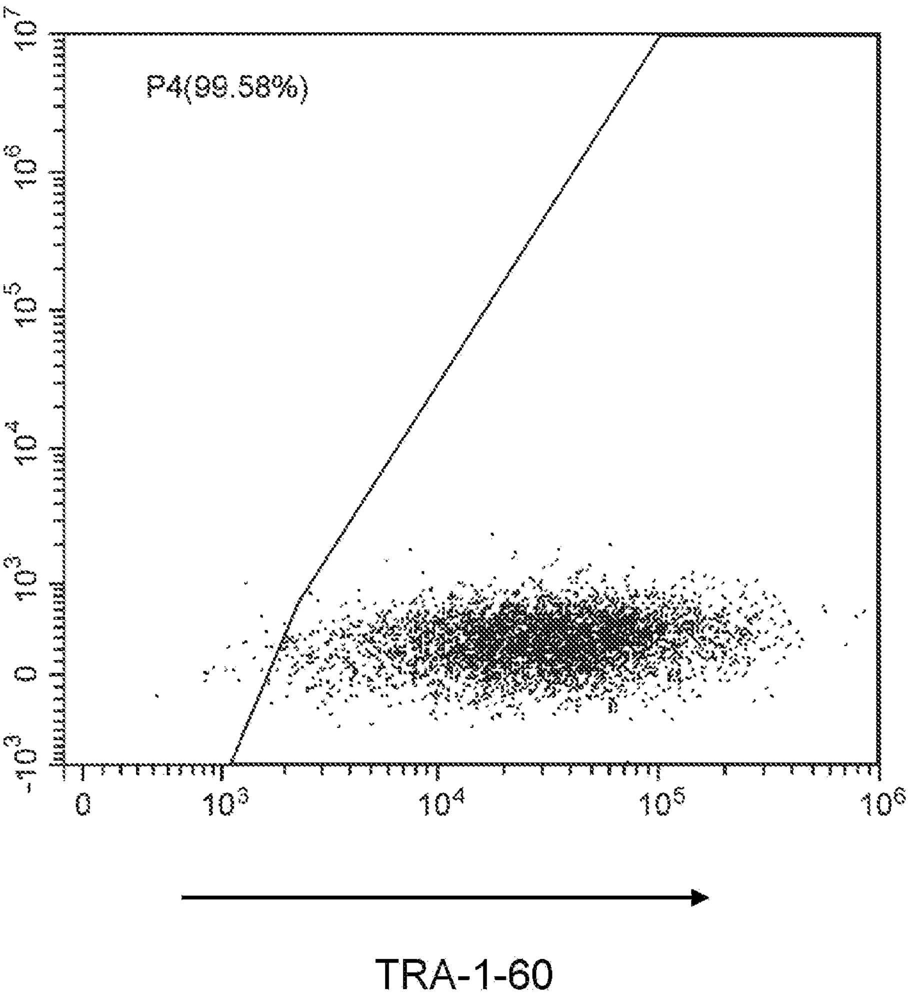
FIG. 16 is a histogram that shows the results of flow cytometric analysis of cells produced by the iPS cell production method according to Example 5.

Fifteen days after the addition of the Sendai virus to the blood growth culture medium, the cells were submitted to observation with a microscope, and the formation of ES cell-like colonies was confirmed as shown in FIG. 15. In addition, the cells were fixed using 4% paraformaldehyde and the expression level of TRA-1-60 cell surface antigen in the fixed cells was measured using a flow cytometer; as shown in FIG. 16, the post-induction cells were approximately 100% TRA-1-60 positive and it was confirmed that almost complete reprogramming had occurred. It was thus shown that cells could be reprogrammed by introducing reprogramming factors into the cells in the cell culture vessel and culturing the reprogramming factor-transduced cells in the same cell culture vessel.

Example 6

A liquid blood growth culture medium that was not a gel was introduced into a laminin-coated flask, and $5\times10^5$ blood cells (mononuclear cells) were seeded. This was followed by introduction of the flask into a 37° C. $CO_2$ incubator, and the blood cells were cultured for 7 days. After this, a Sendai virus vector loaded with OCT3/4, SOX2, KLF4, and cMYC (CytoTune-iPS 2.0, Thermo Fisher Scientific Inc.) was added to the blood growth culture medium to provide a multiplicity of infection (MOI) of 5 and the blood cells were infected with the Sendai virus.

Two days after the addition of the Sendai virus to the blood growth culture medium, the flask was completely filled with stem cell culture medium (DMEM/F12 containing 20% KnockOut SR (registered trademark, Thermo Fisher Scientific Inc.)) or StemFit so air did not remain in the flask; the flask was closed with a cap to prevent gas exchange with the outside; and the interior of the flask was closed off to prevent the permeation of cells, microorganisms, impurities, and so forth.

Figure 17:
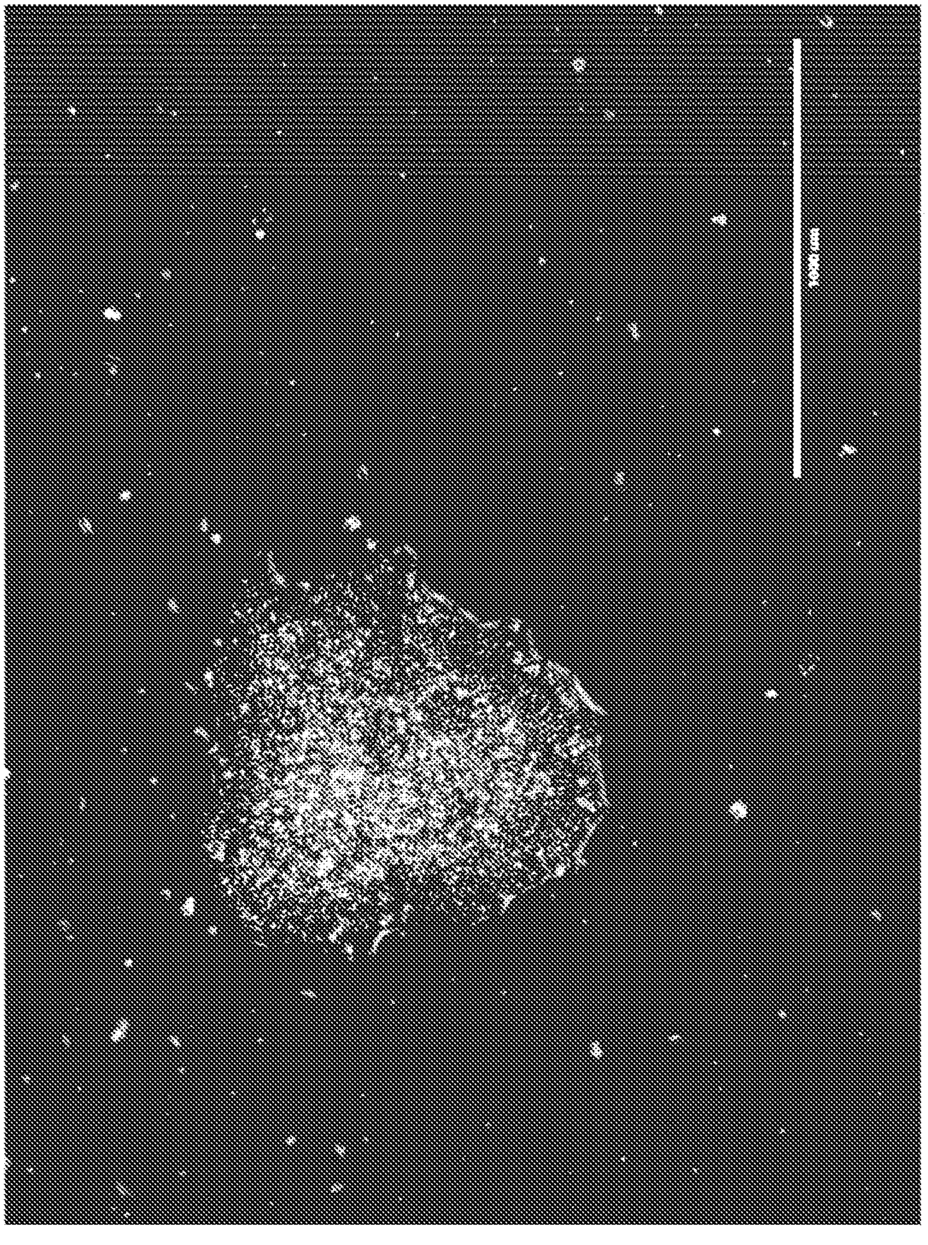
FIG. 17 is a micrograph of cells produced by the iPS cell production method according to Example 6.
Figure 18:
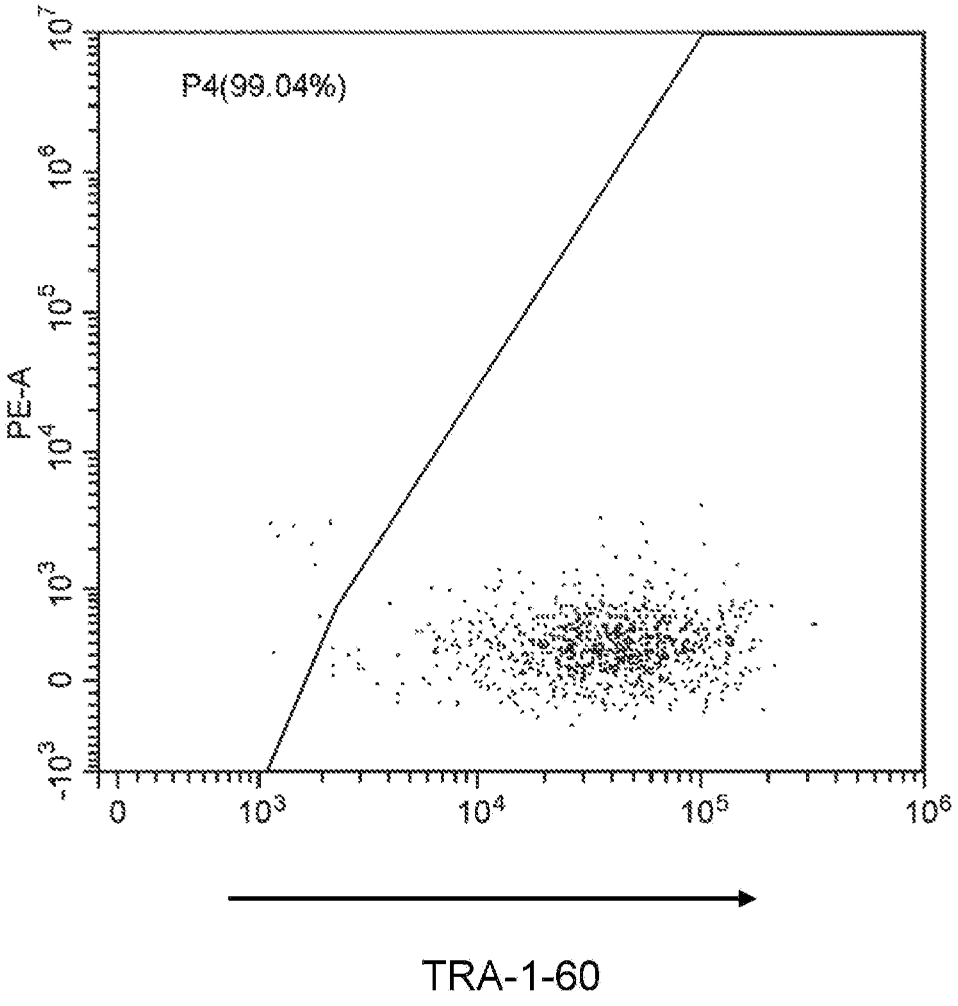
FIG. 18 is a histogram that shows the results of flow cytometric analysis of cells produced by the iPS cell production method according to Example 6.

Fifteen days after the addition of the Sendai virus to the blood growth culture medium, the cells were submitted to observation with a microscope, and the formation of ES cell-like colonies was confirmed as shown in FIG. 17. In addition, the cells were fixed using 4% paraformaldehyde and the expression level of TRA-1-60 cell surface antigen in the fixed cells was measured using a flow cytometer; as shown in FIG. 18, the post-induction cells were approximately 100% TRA-1-60 positive and it was confirmed that almost complete reprogramming had occurred. It was thus shown that cells could be reprogrammed by introducing reprogramming factors into cells in the cell culture vessel and culturing the reprogramming factor-transduced cells in the same closed cell culture vessel.

REFERENCE SIGNS LIST

10 Blood container
11 Erythrocyte removal vessel
12 Flow channel
13 Flow channel
14 Fluid machinery
15 Mononuclear cell collector
16 Flow channel
17 Flow channel
18 Fluid machinery
19 Flow channel
20 Mononuclear cell suction device
21 Fluid machinery
22 Cell culture vessel
23 Flow channel
24 Fluid machinery
25 Culture medium container
26 Flow channel
27 Variable-volume container
28 Fluid machinery
29 Flow channel
30 Variable-volume container
31 Flow channel
32 Culture medium container
33 Fluid machinery
34 Flow channel
35 Variable-volume container
36 Flow channel
37 Fluid machinery
38 Flow channel
39 Flow mechanism
40 Culture medium holding tank
50 Blood container
51 Flow channel
52 Fluid machinery
53 Erythrocyte treatment agent container
54 Flow channel
55 Fluid machinery
56 Flow channel
57 Mixer
58 Flow channel
60 Flow channel
61 Liquid diluent container
70 Vacuum container
71 Vacuum container
100 Erythrocyte removal device
101 Erythrocyte removal device
115 Opening
116 Opening
117 Flow channel
200 Cell culture device

What is claimed is:

1. A cell culture device comprising:
a cell culture vessel for culturing cells;
a first variable-volume container connected to the cell culture vessel;
a first flow channel connecting the first variable-volume container to the cell culture vessel;
a first pump disposed in the first flow channel for transferring a fluid within the first flow channel;
a second variable-volume container connected to the cell culture vessel; and
a second flow channel connecting the second variable-volume container to the cell culture vessel,
wherein the first pump is configured to transfer a fluid within the first variable-volume container into the cell culture vessel through the first flow channel in order to contract a volume of the first variable-volume container and expand a volume of the second variable-volume container,
wherein the cell culture vessel is inset and embedded in a gas-impermeable material, and
wherein an interior of the cell culture vessel is coated with a cell adhesion coating agent such that cells in the cell culture vessel are adherent cultured on the cell adhesion coating agent.

2. The cell culture device according to claim 1, wherein the interior of the cell culture vessel, an interior of the first variable-volume container, and an interior of the second variable-volume container can be closed off from outside air.

3. The cell culture device according to claim 1, wherein the first variable-volume container holds a substance.

4. The cell culture device according to claim 1, further comprising a third flow channel for supplying cells into the cell culture vessel.

5. The cell culture device according to claim 1, further comprising a second pump for supplying cells into the cell culture vessel.

6. The cell culture device according to claim 1, further comprising a fluid container that holds a fluid to be supplied into the cell culture vessel.

7. The cell culture device according to claim 6, wherein the fluid held in the fluid container is a somatic cell culture medium or a stem cell culture medium.

8. The cell culture device according to claim 1, further comprising a temperature control element that controls a temperature in the cell culture vessel.

9. The cell culture device according to claim 1, further comprising a hollow fiber membrane disposed in the cell culture vessel.

10. The cell culture device according to claim 1, wherein the first flow channel connects the first variable-volume container to the cell culture vessel such that cells in the cell culture vessel can be transferred to the first variable-volume container through the first flow channel.

11. The cell culture device according to claim 1, further comprising:
a third flow channel connected to the cell culture vessel; and
a second pump disposed in the third flow channel,
wherein the third flow channel and the second pump are configured such that, at least one of passaging and expansion culture of cells in the cell culture vessel is carried out by suctioning the cells in the cell culture vessel into the third flow channel and returning the cells in the third flow channel to the cell culture vessel by the second pump.

12. The cell culture device according to claim 11, wherein the third flow channel has a meandering structure or has a fluctuating diameter.

13. The cell culture device according to claim 1, wherein the cell culture vessel comprises a member having an inscribed recess, and the recess forms at least a portion of the interior of the cell culture vessel.

14. The cell culture device according to claim 1, wherein the first pump is a reciprocating pump or a rotary pump.

15. The cell culture device according to claim 14, wherein the first pump is a reciprocating pump and is selected from the group consisting of a piston pump, a plunger pump, and a diaphragm pump.

16. The cell culture device according to claim 14, wherein the first pump is a rotary pump and is selected from the group consisting of a gear pump, a vane pump, and a screw pump.

17. The cell culture device according to claim 1, wherein the first pump is a peristaltic pump or a tubing pump.

18. The cell culture device according to claim 1, wherein the interior of the cell culture vessel is directly coated with the cell adhesion coating agent.

19. A cell culture system, comprising:

(a) an erythrocyte removal device comprising:

a blood container for holding blood;

an erythrocyte removal vessel for receiving the blood from the blood container and at least partially removing erythrocytes from the blood; and a mononuclear cell collector for receiving, from the erythrocyte removal vessel, treated blood from which the erythrocytes have been at least partially removed, and for collecting mononuclear cells from the treated blood, wherein the mononuclear cell collector has a funnel-shaped bottom; and (b) the cell culture device of claim 1, wherein the funnel-shaped bottom of the mononuclear cell collector of the (a) erythrocyte removal device is connected to the cell culture vessel of the (b) cell culture device via a third flow channel for transferring the mononuclear cells.

* * * * *